United States Patent [19]
Pellerin et al.

[11] Patent Number: 6,103,506
[45] Date of Patent: Aug. 15, 2000

[54] ENZYME AND MICROORGANISM DEGRADING RHAMNOGALACTURONANE II

[75] Inventors: Patrice Pellerin; Jean-Marc Brillouet, both of Montpellier; Thierry Doco, Saint-Georges-d'Orques; Pascale Williams, Montpellier; Stephane Vidal, Montpellier; Michel Moutounet, Montpellier, all of France

[73] Assignee: Institute National de la Recherche Agronomique, France

[21] Appl. No.: 08/973,335

[22] PCT Filed: May 21, 1996

[86] PCT No.: PCT/FR96/00758

§ 371 Date: Jan. 26, 1998

§ 102(e) Date: Jan. 28, 1998

[87] PCT Pub. No.: WO96/37604

PCT Pub. Date: Nov. 28, 1996

[30] Foreign Application Priority Data

May 23, 1995 [FR] France .................................. 95 06142

[51] Int. Cl.$^7$ ................................ C12N 9/24; C12N 1/20; C12N 9/00; C12P 19/14

[52] U.S. Cl. ............................ 435/183; 435/99; 435/200; 435/256.3

[58] Field of Search .............................. 435/183, 99, 200, 435/256.3

[56] References Cited

PUBLICATIONS

Stevenson et al Plant Physiol. (1986) 80, pp. 1012–1019, 1986.

*Primary Examiner*—Herbert J. Lilling
*Attorney, Agent, or Firm*—Bierman, Muserlian and Lucas

[57] ABSTRACT

Enzyme degrading rhamnogalacturonane II (RG-II) having an endo-β-L-rhamnopyranosyl-(I→3')-D-apiofuranosyl hydrolase activity and/or an endo-α-L-fucopyranosyl-(I→4)-L-rhamnopyranosyl hydrolase activity. This enzyme can be produced by a microorganism, especially of the penicillium species, such as the branches 1-1577 and 1-1578 lodged with the CNCM. The RG-II can obtained from plant extracts by means of a method comprising a chromatography stage.

6 Claims, 16 Drawing Sheets

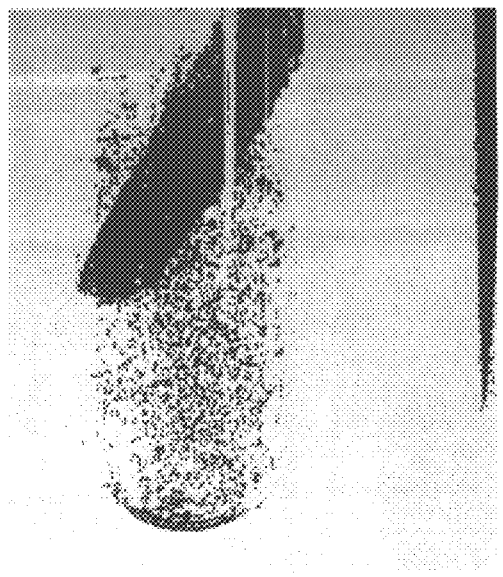
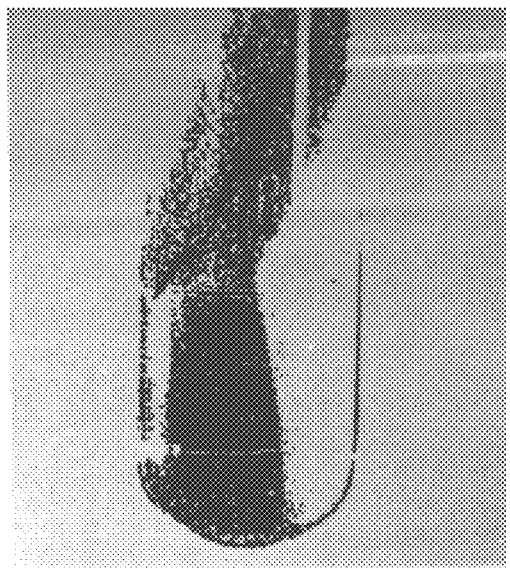
FIG. 20A                    FIG. 20B
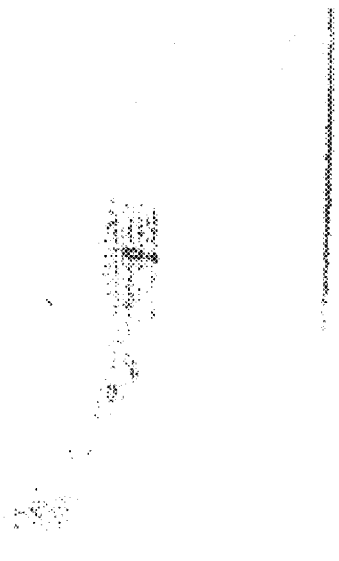
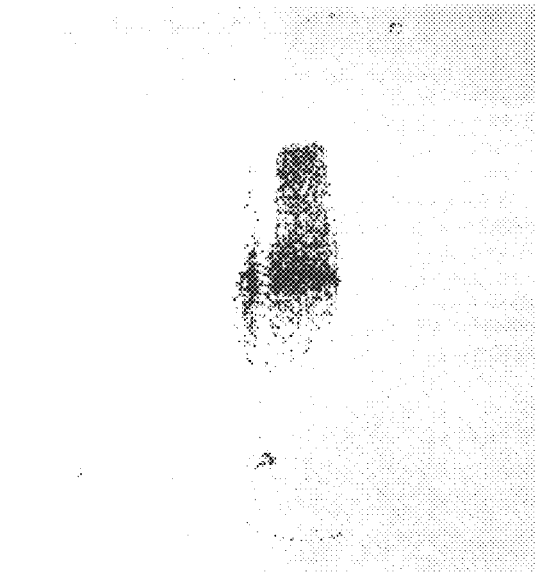
FIG. 20C                    FIG. 20D

ENZYME AND MICROORGANISM DEGRADING RHAMNOGALACTURONANE II

The present invention concerns an enzyme degrading rhamnogalacturonane II (RG II) and its derivatives and the method for obtaining said enzyme.

It further concerns a method for obtaining RG-II.

It also concerns the use of said enzyme.

Rhamnogalacturonane II is a universal and highly complex constituent of the cellular wall of plants (O'Neil et al., Methods in Plant Biochemistry (1990) 2:415–439)). It belongs to pectic polysaccharides and is mainly present in the average lamelle and the primary wall.

Its structure is extremely complex (FIG. 1) since it is composed of 12 different monosaccharides for one degree of polymerisation (dp) close to 30. This complexity is strengthened by the presence of rare sugars in its composition which contains apiose or 3-C-(hydroxymethyl)-D-glycero-tetrose, KDO or 2-ceto-3-deoxy-D-manno-octulosonic acid, DHA or 3-deoxy-D-lyxo-2-heptulosaric acid, 2-O-methyl-fucose, 2-O methyl-xylose and finally acetic acid or 3-C-carboxy-5-deoxy-L-xylose. This latter monosaccharide constitutes a specific marker of RG-II. More usual monosaccharides in parietal polysaccharides, rhamnose, fucose, arabinose, galactose and galacturnonic and glucuronic acids are also present in the composition of RG-II, but most often with anomeries and types of particular and multiple links which reinforce the specificity and complexity of the molecular structure.

The ultrastructural organisation of RG-II (FIG. 1) further increases this complexity (Puvanesarjah et al., Carbohydr. Res. (1991) 218:211–222)). A homologue chain composed of between 7 and 14 galacturonic acid residues linked at $\alpha$-(1→4) carries at still not determined positions 4 different branches: two dissacharides and two more complex or nonsaccharide chains. Structural variabilities are observed for the length of the homogalacturonic chain and for the extremity of the branch B and seem due the enzymatical activities used to obtain it. Secondly, the presence of unidentified substituents has been detected on the A5 residue in addition, the RG-II molecule contains 2 to 3 methyl groups which esterify the carbolic groups of galacturonic acids and two acetyl groups situated on R3 (aceric acid) and B4 (2-O-methly-fucose) residues.

Thus, the structure of RG-II has been generally determined, even if the nature of certain substituents has still not been identified.

In the cellular wall of plants, RG-II is associated with native pectins, but the exact type of link between protopectin and RG-II is still unknown. Similarly, its role in the wall of vegetables is poorly known. However, it is known that it is present throughout the vegetation world (Albersheim et al., Biochem. Soc. Transactions (1994) 22:374–378); pteridophytes with spermotophytes, gymnosperms with angiosperms, monocotyledons with dicotyledons (FIG. 2) and in significant qualities in the average lamalla of the walls. It is also known that its structure is preserved in the different plants which have been studied (Albersheim et al., Biochem. Soc. Transactions (1994) 22:374–378)).

Recent studies have showed that it could act as a signal polysaccharide and induce specific responses from the plant (elicting activity) (Aldington and Fry, Exp. Botany (1994) 45:287–293). However, its abundance and omnipresence and complexity of its structure leave one to assume that it plays a fundamental role in the cohesion of the cellular walls of plants and thus in the cellular organisation of tissue systems.

RG-II is freed from the cellular walls under the action of enzymes with pectolytic activity (esterase pectin, endo- or exo-polygalacturonase) which degrade the smooth chains of native pectins and free RG-II in a non-degraded form (Darvill et al., Plant Physiol. (1978) 62:418–422), as shown on FIG. 1. The variability of the length of the homogalactronic chain accounts for the enzymatical degradations which have enable it to be freed from native pectins (Whitcombe et al., Carbohydr.Res (1995) 271:15–29).

The complexity and originality of the structure of RG-II render it particularly resistant to degradation by the enzymes present in the extracts of plants as in commercial enzyme fungal or bactericide preparations.

No degradation activity can in fact be observed in commercial enzymatical preparations for degrading the walls of plants richest in various activities. The only degradations observed concern the arabinofuranose, rhamnopyranose or galactopyranose residues situated at the non-reducing extremity of the lateral chains. Exo-enzymes enabling these residues to be freed in fact currently exist on enzymatical preparations and, according to the authors, thus undoubtedly explains the variability observed between the reported various preparations of RG-II.

When pressing or crushing fruit and vegetables, pectolytic activities are freed which ensure the degradation of the homogalacturonic chains of native pectins. These activities are reinforced by adding commercial pectolytic enzymes and by the fermentation flora when wines or fermented products are used. The RG-II is freed in an intact form and in often significant quantities in fruit juices and nectars, vegetables and derived substances and in particular in wines.

In wines, RG-II represents one of the major polysaccharides (Doco and Brillouet, Carbohydr. Res. (1993) 243:333–343), its concentration possibly reaching 100 mg/l. It takes part in a large number of undesirable phenomena, such as clogging up of the filtering membranes (Belleville et al., Enol. Vitic. Sci (1991) 46:100–107), the formation of unstable complexes with other colloidal macromolecules and the induction of precipitation phenomena. It has to be eliminated by using special enzymes able to degrade it.

To date, several methods for obtaining RG-II from wine have been described:

by enzyme hydrolysis with the aid of fungal endopolygalacturonases of cellular walls separated from cultures of vegetable cells in suspension (Darvill et al. Plant Physiol. (1978) 62:418–422), from a commercial enzymatical preparation of *Aspergillus niger*, AC pectinol (Stevenson et al., Carbohydr. Res (1988) 179:269–288). The RG-II is present there in a low concentration and its purification involves a large number of stages for eliminating the proteins and the colouring matter, from wine (Doco and Brillouet, Carbohydr. Res (1993) 243:333–343) and the purification described makes use of 4 successive steric exclusion and ion exchange chromatographic stages.

It should be noted that the rhamnogalacturonane I or RG-I, although having a extremely similar name, is a constituent of vegetable cellular walls totally different from RG-II both as regards its structure (its structure is based on an alternation of rhamnose and galacturonic acid) and its degradation by the enzymes. Rhamnogalacturonase (Schols et al., Carbohydr. Res. (1990) 206:105–115) or protopectinase (Sakamoto and Sakal, Carbohydr. Res (1994) 259:77–91) activities have already been described.

The above analysis of the state of the art shows that there is no enzyme or enzymatical preparation possessing a satisfactory activity for degrading RG-II. However, the presence of this polysaccharide is a source of undesirable phenomena, such as clogging of the filtering membranes, the formation of unstable complexes with other colloidal macromolecules and the induction of precipitation phenomena.

Owing to the extent of the economic activities involved, it was essential to find a solution to this problem.

The applicant showed that it was possible to isolate the enzymatical activities responsible for degrading the RG-II and its derivatives from microorganisms.

Firstly, he set up a new method for obtaining RG-II making it possible to obtain it in large quantities from various vegetable sources.

The present invention concerns an enzyme characterised in that it degrades RG-II and its derivatives.

According to the present invention, by RG-II is meant any polysaccharide comprising the structure shown in FIG. 1, whether under the form of a monomer or a dimer, and any molecule resulting from its partial degradation and comprising at least one frament of chaim A, B, C or D, which is characteristic both as regards its composition and its sequence.

In the following, when reference is made to RG-II the same also applies to any derivate of this molecule.

Such enzyme advantageously exhibits an endo-hydrolase type of activity.

This enzyme may in particular exhibit an endo-β-L-rhamnopyranosyl-(1→3')-D-apiofuranosyl hydrolase and/or endo-α-L-fucopyranosyl-(1→4)-L-rhamnopyranosyl hydrolase activity. These activities may be identified by their capacity to free the chain A, as shown in FIG. 1.

This enzyme can be produced by a micro-organism and in particular a mushroom of the species Pencillium.

These microorganisms having activity for degrading RG-II constitute another object of the present invention. In particular, they may be the following Pencillium branches lodged on May 19, 1995 with the National Collection of Cultures of Microorganisms of the Pasteur Institute (CNCM):

branch of *Pencillium simplicissimum* lodged with the CNCM under the n° 1=1577 (IPV1), branch of *Pencillium dateae* lodged with the CNCM under the n° 1-1578 (LaV2).

These two branches of mushrooms exhibit a characteristic aspect of fibrous mushrooms partitioned with fast formation (as from the 6th culture day) with blue-green spores.

*P. dateae* is a rare mushroom still isolated from forest soils and which is known for its capacity to degrade amidon and pectic polysaccharides. This species has been described in <<Compendium of Soil Fungi, H. K. Domsch, W. Gams and T. H. Anderson (1980) Academic Press, London, page 560.

*P. simplicissimum* is more common and frequently isolated from decomposing vegetables. This species has been described in <<Compendium of Soil Fungi, H. K. Domsch, W. Gams and T. H. Anderson (1980) Academic Press, London, pages 597–588>>.

The present invention also concerns enzymatical preparations containing an enzyme degrading RG-II and its derivatives as described above.

The enrichment of these preparations with activities enabling RG-II to be degraded offers an entirely new potential for all those applications requiring partial or total degradation of the cellular walls and polysaccharides of plants.

Enzymes able to specifically degrade RG-II and its derivatives may in particular be used in the following applications:

elimination of RG-II from fruit juices, vegetables and their derivatives so as to improve filterability, facilitate the production of juices and concentrated aromatic bases, favour clarification phenomena and ensure good stability of the finished products, cleaning of micro- and ultra-filtering membranes used for clarifying fruit juices, vegetables and their derivatives, obtaining maceration type preparations, that is allowing cellular tissues of young vegetables to be separated with a minimum degradation of the parietal structures (production of fruit nectars, purees, jellies and vegetable and fruit concentrates), obtaining liquefying type preparations, that is before providing full hydrolysis of the polysaccharides of the cellular walls of plants (production of juices and fruit aromatic bases, vegetables and fermented drinks, beer), production of pectins and foods for animals from vegetable residues (beetroot pulps, solid residues after fruit pressing . . . ), production of cellulose from vegetables; enzyme hydrolysis of other polysaccharide constituents makes it possible to improve production yields (textile industry, paper production).

The commercial enzymatical preparations enabling the cellular walls of plants to be degraded needs to possess the most specific and best possible defined biochemical modes of action according to the desired type of use. The specific contribution of enzymes for degrading RG-II and having specific well-defined modes of action shall improve exploitation of the technological potentials of fungal enzymes.

The above-described enzymes and enzymatical preparations of the invention may preferably be obtained by a method including the following steps:

culturing microorganisms exhibiting a degradation activity of RG-II or of its derivatives, in a suitable culture environment adapted to the production of such enzymes, collecting the enzyme or enzymatical preparation in the culture supernatant or the supernatant from the crushed from the crushed micro-organisms.

Preferably, such method comprises the following steps:

culturing microorganisms exhibiting a degradation activity of RG-II in a suitable culture medium adapted to these micro-organisms and containing RG-II, recovery of the micro-organisms, crushing of the micro-organisms, removing of the insoluble material, in particular by filtration or centrifugation of the crushed micro-organisms, and recovery of the supernatant containing the enzymes or the enzymatical preparation.

The enzymes can also be directly obtained from the supernatant of the culture without crushing the micro-organisms when conditions allow to do so, by choosing the conditions or the branches so that the enzymes are freed in the medium.

This method is advantageously implemented by using branches of Penicillium fided with the CNCM under the N° 1-1577 and N° 1-1578.

These enzymes may also be obtained by genetic engineering after cloning of the gene(s) responsible for their synthesis or by any other suitable technique known to those skilled in the art and in particular by synthesis from isolated amino acids after having identified their sequence.

The present invention also relates to a method for obtaining RG-II and its metabolites or derivatives from a vegetable extract, wherein it comprises a chromatography stage of the extract.

Obviously, this method concerns the obtaining of RG-II, but also products known as metabolites for degrading this molecule which could form when implementing this method, as well as all RG-II derivatives.

According to the present invention, by <<vegetable extract>> is meant any preparation containing in particular solubilised vegetal polysaccharides. The polysaccharides may have undergone a concentration step, either by ultrafiltration or by precipitation, for example with ethanol, methanol or any other suitable solvent.

This method can also comprise at least an adsoprtion chromatography of RG-II on a RG-II retaining carrier. Such adsorption chromatography can be carried out on an active carbon, a polystyrene/divinylvenzone resin or on any other suitable support.

There may also be added, before and/or after the chromatography stage, a stage of separating the polysaccharides, either by ultrafiltration, or by steric exclusion chromatography. For implementing the fractionated precipitation, ethanol or methanol is advantageously used. For implementing the steric exclusion chromatography, a <<Sephacryl>> column or any other suitable carrier is advantageously used.

The present invention also concerns preparations which can to be obtained by one of these methods:

firstly, preparations mainly containing (that is at least 95%) RG-II monomers, and secondly preparations containing at least 80% and preferably more than 95% RG-II dimers.

After each chromatography, those fractions containing RG-II are determined on the basis of their compositions. This operation can be carried out by those skilled in the art.

These methods are easily able to obtain preparations in considerable quantities (about one kilogram) of RG-II from any vegetable products, except for those derived from graminaceous plants, such as fruit juices, vegetables and their derivatives, in particular wine, possibly concentrated, slops and grape musts, on a scale of about ten grams. The RG-II is preferably obtained from the primary walls of plants but it can be also isolated from any plant derivative product requiring a solubilisation of the walls, either during conventional transformation process (pressing, fermentation) or by treatment with liquefaction enzymes.

A further object of the invention is a method for screening micro-organisms, especially mushrooms, for their capacity to degrade RG-II, said method being characterised in that the micro-organisms are grown on a suitable medium and containing RG-II.

It also concerns a culture medium for these micro-organisms containing RG-II.

The methods of the present invention and in particular the methods for preparing and isolating enzymes according to the present invention, as well as the method for preparing RG-II, can be implemented by those skilled in the art on the basis of a mere reading of the present description and general information. Nevertheless, reference could be made to the following manual: Methods in Microbiology, volumes 1 to 6, J. R. Morris and D. W. Ribbons (1969–1972), Academic Press, London, New York.

The present invention is now illustrated without being limited thereby, by the following examples.

BRIEF DESCRIPTION OF THE DRAWINGS

The figures referred to in the present description and its example are as follows.

(FIG. 19B).

FIGS. 19C, 20A and 20C respectively represent the degradations by the enzymatical extracts of the IPVI branch of carrot, apple and potato tissues by comparing them with the respective references (FIGS. 19D, 20B and 20D).

EXAMPLE 1

Purification of Rhamnogalacturonane II by Anion Exchange Chromatography and Molecular Screening From Wine The RG-II is present in a non-degraded form, especially in fruit juices, vegetable juices and their derivatives, especially fermented derivatives. The RG-II can be purified with homogeneity from any products derived from plants by carrying out the following purification stages:

1. Obtaining macromolecules in one stage by precipitation with 80% ethanol or by ultrafiltering.
2. Acid pH anion exchange preparative chromatography.
3. Molecular screening chromatography (this stage making it possible to arrive at a high purity percentage can be ignored if a purity rate of 80% of the RG-II preparation is sought).

1—Wine sample and obtaining of colloids

The wine used has been obtained from black Carigan cropped at maturity in September 1991 in the Pech-Rouge/Narbonne Domain experimental. 600 liters have been concentrated on a Carbo Sep M5 (Tech Sep, France) ultrafiltering membrane with a cut-off threshold of 10,000. The total colloids of the concentrated wine (final volume 25 L) were then precipitated by adding 4 volumes of acidified ethanol to 60 mM Hcl, successively washed with 80 to 90% ethanol, placed back in the water and dialysed against a 40 mM, pH 4.6; sodium citrate buffer. The dry weight of the total colloids (determined after desalinisation and freeze-drying of an aliquot fraction) represented 296 g, namely about 0.5 g per liter of wine.

2. Anion Exchange Chromatography

Figure 1:
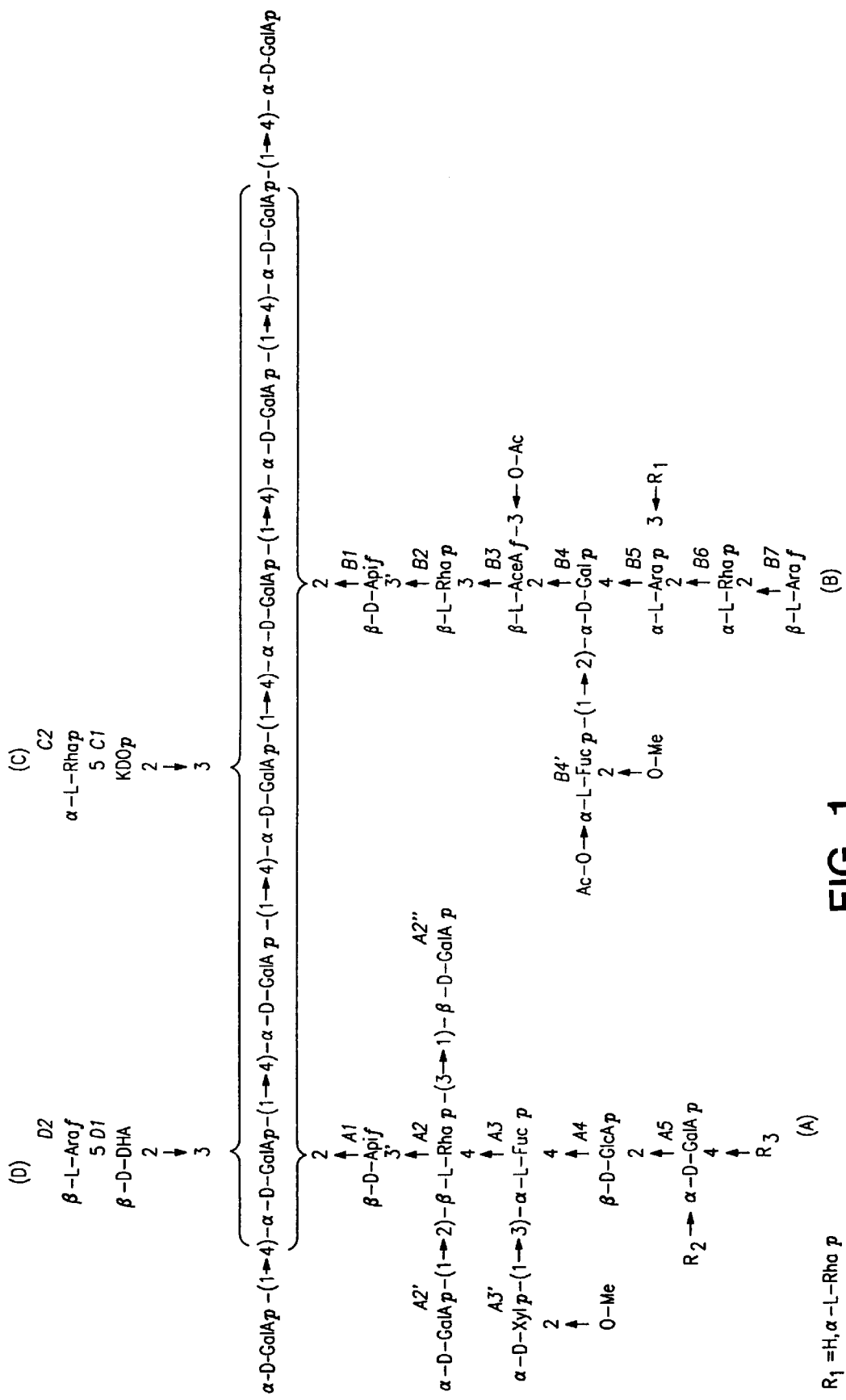
FIG. 1 diagrammatically represents the structure of RG-II including its four lateral chains A to D. On this figure, $R^1$ represents a hydrogen or an α-L-rhamnopyranose and $R^2$ and $R^3$ represent a hydrogen or another substituent.
Figure 2:
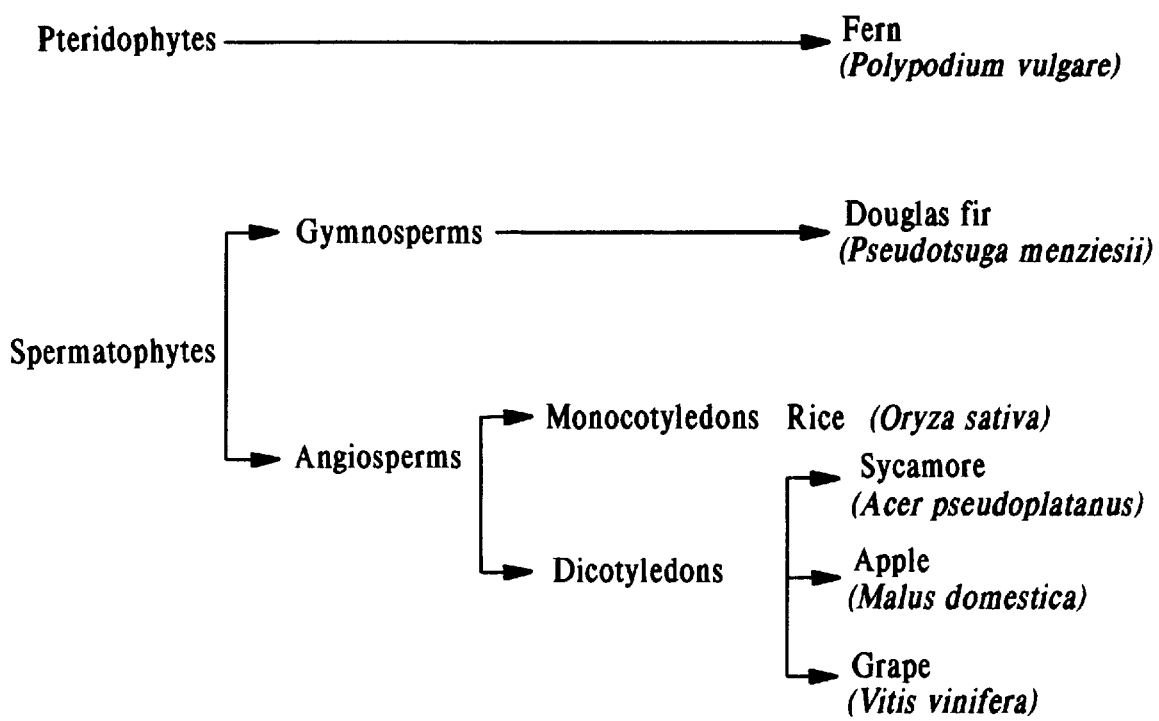
FIG. 2 illustrates the distribution of RG-II in the vegetable kingdom.
Figure 3:
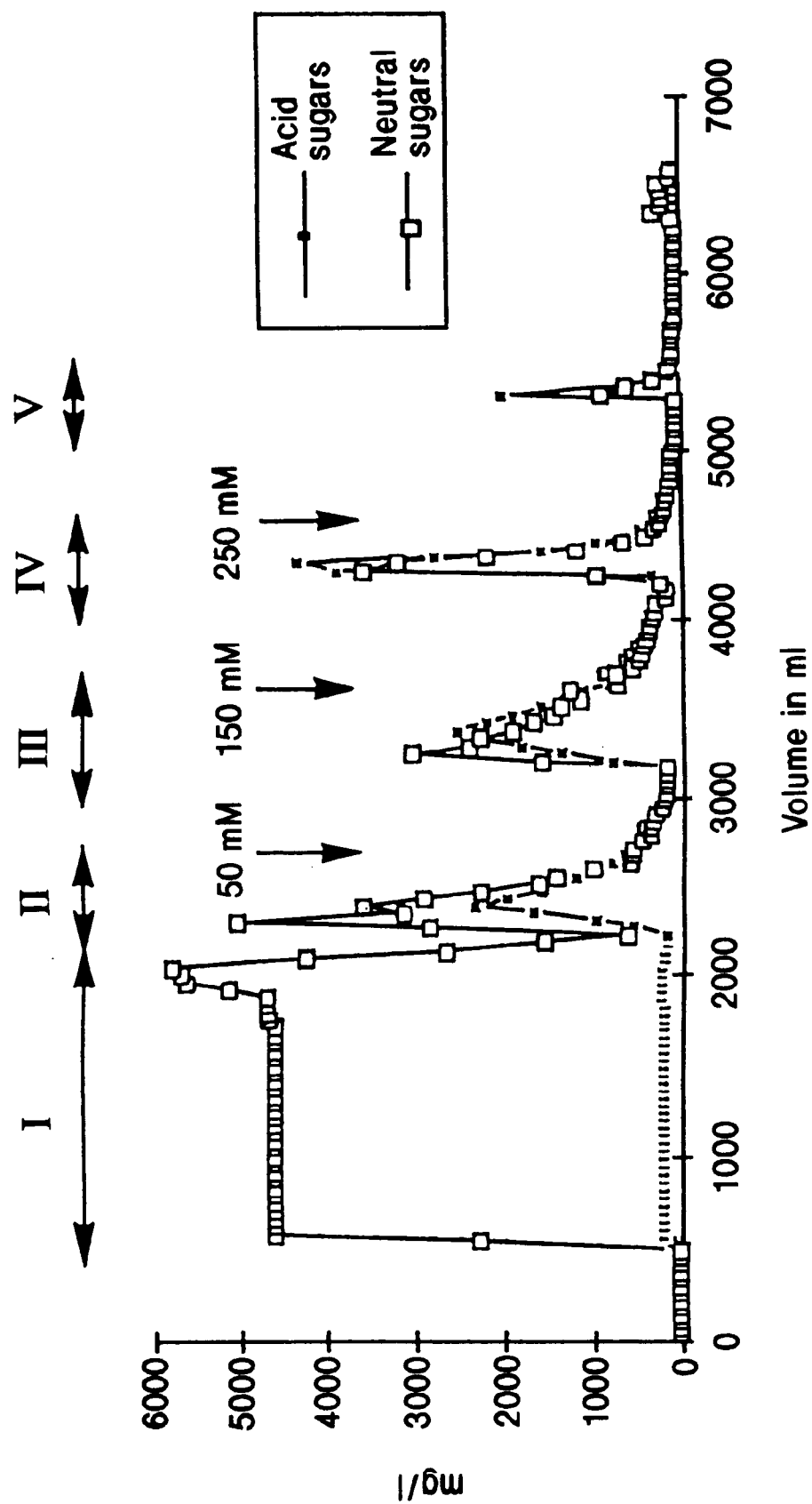
FIG. 3 illustrates the fractionating of polysaccharides, acid sugars and neutral sugars of a wine on a DEAE column (Macroprep).

The colloids solution with pH 4.6 has been fractionated by anion exchange chromatography by 10 successive passages on a DEAE-Macroprep (BioRad, USA) column (5×80 cm) balanced to 20.5 ml/min in a 40 mM, pH 4.6, sodium citrate buffer. The neutral or slightly charged polysaccharides have been eluted in the injection buffer (fraction I). The fractions containing the RG-II have been firstly eluted via passage of the 50 mM citrate buffer concentration (fraction II) and then via the addition of 50 (fraction III) and 150 mM (fraction IV) of NaCl to the elution buffer (FIG. 3). These three fractions respectively represented 7.9%, 6.6% and 4.1% of the total colloids expressed as dry weight.

3. Purification of RG-II With Homogeneity by Steric Exclusion Chromatography The RG-II present in the fractions II and III has been purified with homogeneity by steric exclusion chromatography on a Sephacryl S-400 HR column (5×75 cm) balanced to 7 ml/min in a 50 mM, pH 5, sodium acetate buffer containing 50 mM of NaCl.

The fractions containing the RG-II have been finally dialysed against water prior to freeze-drying.

Figure 4A:
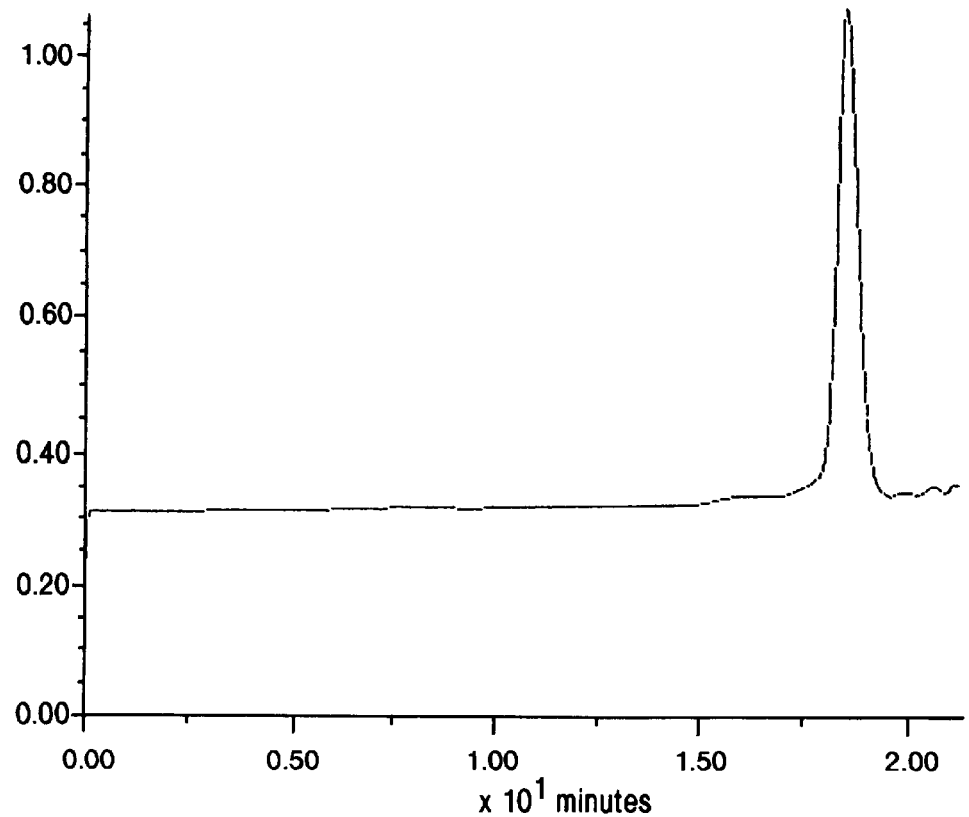
FIGS. 4A and 4B are high-performance steric exclusion chromatography profiles of two RG-II fractions isolated from a red wine.
Figure 4B:
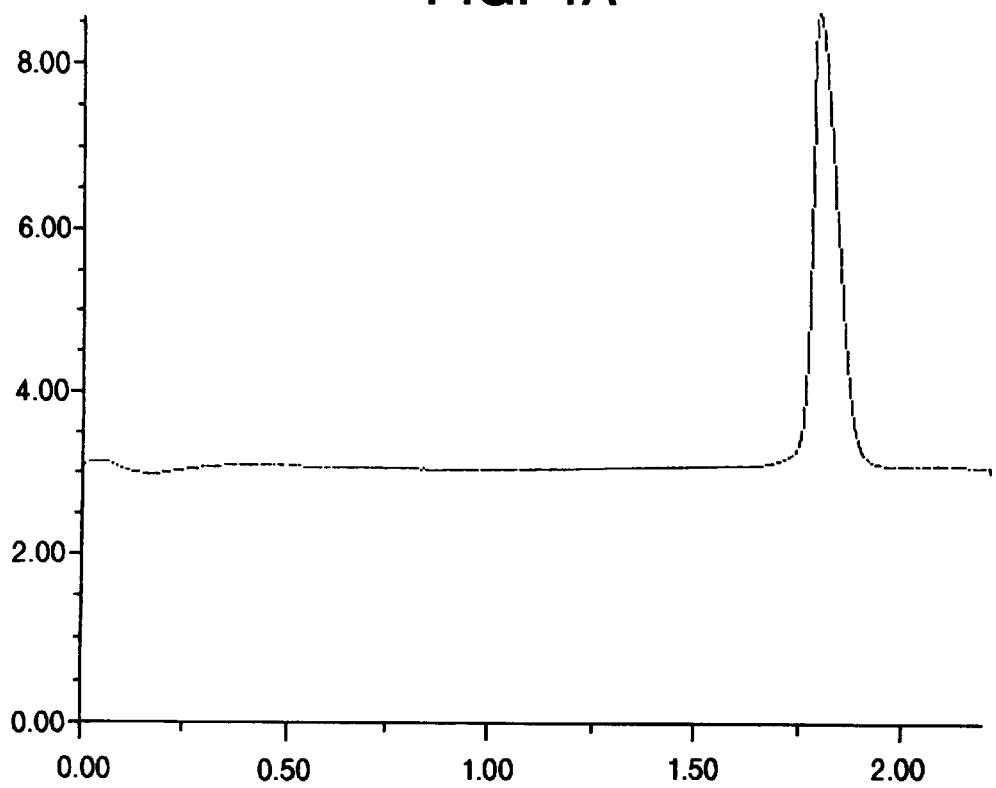

The two RG-II samples obtained had a perfectly homogeneous high-performance steric exclusion chromatography profile (CES-HP, analysed on two Shodex OHPak KB-803 and KB-805 columns in series, eluting 0.1 M LiNO3 at 1 ml/min, refractometric detection) (FIG. 4) and respectively represented 4.4 and 4.6% of the total colloids of the wine sample. The total percentage of RG-II of the wine sample used was more than 50 mg/l since it was necessary to add to it the RG-II contained in fraction IV which had not been purified with homogeneity.

4. Compositions of Purified RG-II Fractions From the Wine

The two purified RG-II fractions each had the characteristic composition-of the RG-II (table 1). As regards an analysis of their composition, they do not differ from each other significantly.

Figure 5:
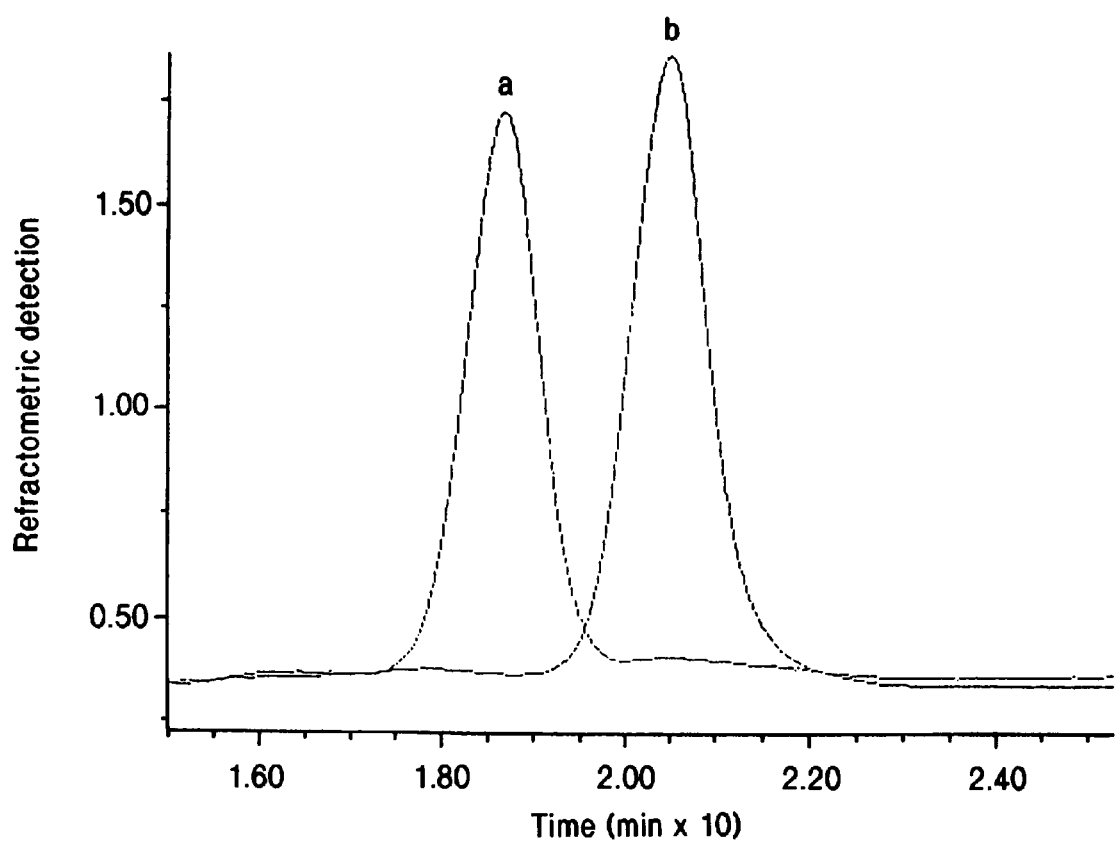
FIG. 5 shows a high-performance steric exclusion chromatography profile on a Superdex-75 HR column of two RG-II fractions purified from wine concentrate: a: fraction III, RG-II dimer (molecular mass 9500 Da, elution at 18.5 min); b: fraction II, RG-II monomer (molecular mass 4750 Da, elution at 20.5 min).

The fractions II and III obtained on DEAE-Macroprep were analysed on a Superdex-7511R column (1×30 cm, exclusion at 14 min), a molecular screening support. This analysis (FIG. 5) reveals that the fraction II mainly includes RG-II monomers (elution at 20.5 min, molecular weight 4750 Da), whereas fraction III contains more than 95% RG-II dimers (elution at 18.5 min, molecular weight 9500 Da).

The RG-II preparation of the fraction II was accordingly used for screening and the induction of enzymatical activities with specific degradations.

EXAMPLE 2

RG-II Obtained by Adsorption Chromatography From Slops

The slops used have been obtained by under-vacuum distilling and concentration of 300 hl of red wine (mixture of wines from several vines):

The slops obtained by means of distilling have been concentrated by evaporation under vacuum on a falling float system. The bitartrate salts are eliminated after decanting in this concentrate and then the slops are reconcentrated on the same system. Overall, the wine has been concentrated 30 times and the total colloids of the 1000 liters of concentrated slop obtained have been precipitated by adding 4 volumes of 90% ethanol. The precipitate is placed back into 300 liters of water so as to constitute the slops solution used as an RG-II source.

Adsorption Chromatography

The follow-up of the chromatographic separations is ensured by CLHP on Shodex columns (see example 1 or on a Superdex-HR 75 (Pharmacia; flowrate 0.6 ml/min) coupled to a refractometric detection system.

(a) On Activated Carbon

The activated carbon possesses high adsorption capacity with regard to a large number of molecules. In the present invention, the activated carbon has been retained for its ability to separate RG-II from the various categories of pectic polysaccharides. In fact, all the polysaccharides are adsorbed on the active carbon, but the RG-II is desorbed at alcohol concentrations of less than 40%. Two types of carbon have been tested.

Pulverulent Activated Carbon

One liter of a slops solution diluted by one fifth has been placed in contact with 100 grams of powdered activated carbon (Norit® SA*) for 30 minutes. The solution is then sintered-filtered so as to eliminate the carbon particles. The carbon retained on the filter is placed in suspense in 1 liter of 40% ethanol and the mixture is agitated regularly for 30 minutes and then filtered under vacuum. The eluted RG-II is then analysed by CLHP. The composition analysis of this fraction (table 2) indicates a degree of purity approaching 50% for the RG-II.

Extruded Activated Carbon

This type of carbon requires a much longer contact time (48 hours) with the slops solution so as to adsorb the RG-II, but does have the advantage of facilitating the filtering stages. Secondly, the carbon mass required is double that of the pulverulent carbon.

One liter of a slops solution diluted to one fifth has been placed in contact with 200 grams of extruded activated carbon (Norit® RO-08 Supra) for 48 hours. After eliminating the nonadsorbed fraction, the fraction containing the RG-II has been desorbed by dissolving it in 40% ethanol for 24 hours. The RG-II obtained exhibits the same degree of purity as in the case of using the pulverulent carbon.

(b) On a Mixed Polystyrene-divinylbenzene Resin
(Resin Relite® DIAION® SP411)

The Relite® DIAION® SP411 resin is a non-polar synthetic resin composed of polystyrene-divinylbenzene copolymers. It retains the RG-II at the expense of the other polysaccharides present in the plant extracts. These extracts shall therefore be separated into 2 fractions by means of adsorption chromatography on a Relite® DIAION® SP411 resin: one non-retained fraction containing the different polysaccharides of the RG-II and one fraction retained containing the RG-II.

Purification of RG-II on a Pilot Scale

Figure 6:
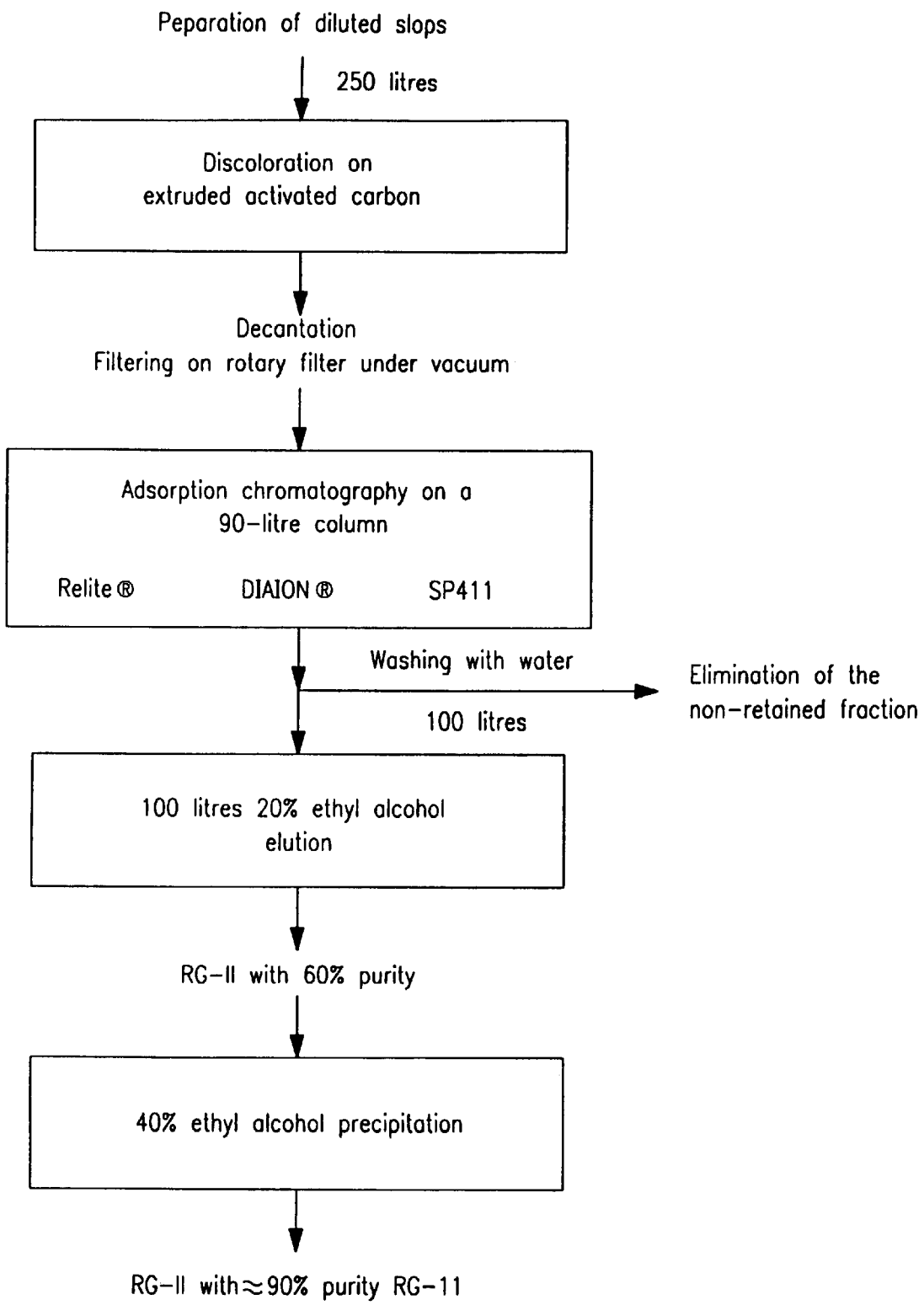
FIG. 6 is a pilot scale RG-II purification diagram.

The pilot scale diagram of purification of RG-II from the slops is shown on FIG. 6. 250 liters of a slops solution diluted to one fifth (2.5 column volumes) have been rapidly discoloured on Norit® RO-08 Supra activated carbon and then moved onto a 90 liter Relite® DIAION® SP411 column with a flow-rate of 40 l/I hr (contact time of 2 hours for an adsorption of the RG-II on this chromatographic support). The column has been washed with 100 liters of water. The non-retained fraction is thus constituted by the volume of injection and washing. The elution of the RG-II has been obtained via the passage of 100 liters of 20% ethanol followed by a washing of the column with 200 liters of water.

The RG-II obtained as above (1 kg for the total slops preparation) exhibits a degree of purity approaching 60% (table 2). The RG-II has been precipitated by adding ethanol (final concentration of about 40% of ethanol). The precipitate obtained contains RG-II with a degree of purity of 90%.

EXAMPLE 3

Obtaining of RG-II by Adsorption Chromatography From Wines

Wine (red wine, vine variety Merlot 94, Chardonnay 94 white wine) has had its alcohol content removed and concentrated twice by evaporation under vacuum on a rotary evaporator.

Figure 7:
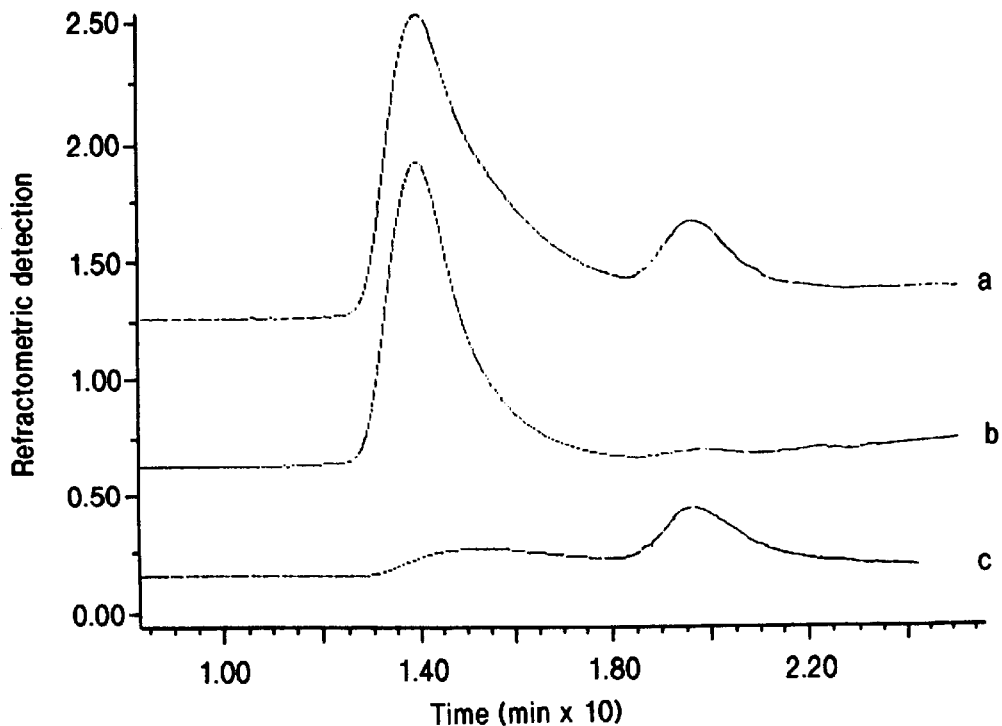
FIG. 7 is a comparison of the profiles determined at CES-HP on a Superdex-75 HR column of the total polysaccharides of a red wine (a) with the non-retained fraction on Relite® DIAION® resin (b) and retained and then eluted with 20% ethanol (c).

Fractions of 15 ml are charged onto 50 ml of Relite® DIAION® SP411 at 25 ml/hr. Then the column is washed with 50 ml of water. The RG-II is then eluted with 50 ml of 20% ethanol and the column is washed with 100 ml of water. The CLHP analysis (FIG. 7) shows that the RG-II is adsorbed quantitatively on the resin since it is absent in the nonretained fraction on the resin and is recovered quantitatively by means of elution with 20% ethanol. The degree of purity of the RG-II solution approaches 50% for the red wine (Table 2) and 35% for the white wine.

EXAMPLE 4

Obtaining RG-II From Grape Must

Amberlite® XAD 2 is a non-polar polystyrene-divinylbenzene copolymer resin. 100 ml of white grape must obtaining by crushing of Grenache variety berries have been injected onto a 100 ml XAD2 resin column balanced in water. The RG-II has been eluted by a 60% volume of methanol with a degree of purity of about 40%. The results of the analysis of the eluates are shown on table 2.

EXAMPLE 5

Obtaining RG-II From Fruit and Vegetable Juices

Soluble extracts have been obtained from 0.6 kg of apples, tomatoes and carrots peeled and diced in 200 ml of ascorbic acid (final concentration 3 mM). The fruit and vegetable juices used have been obtained by means of enzymatical liquefaction via the combined actions of commercial liquefying enzymatical preparations (Pectinex® Ultra SPL; Novo Ferment and Rapidase® Liq; Gist-Brocades) for 24 hours at 45° C. The liquefaction reaction is stooped by the denaturation of the enzymes under the effect of heat. The solid residues have been eliminated by hydro-extraction and the surface floating substance has been used as an RG-II source.

Purification of RG-II of Fruits and Vegetables After Enzymatical Liquefaction

The fruit and vegetable juices obtained by enzymatical liquefaction are filtered on a paper filter before being moved onto a column (2.5×30 cm) balanced with water containing 50 ml of Relite® DIAION® SP411 at 25 ml/hr. the column is washed with 50 ml of water prior to eluting the RG-II with 50 ml of 20% ethanol followed by a washing of the column with 100 ml of water.

The RG-II preparations obtained exhibit degrees of purity exceeding 80%.

The results of their analyses appears in table 2.

EXAMPLE 6

Screening of Micro-organisms Degrading RG-II in a Monomer Form

The RG-II is a universal constituent of the cellular walls of plants and its degradation into the biosphere is ensured by the microorganisms of natural ecosystems: soils, composts, sludge from sewerage plants.

From natural samples, two mushroom branches have been isolated belonging to two species of Penicillium which use RG-II as a sole source of carbon and energy.

1. Culture Medium

The culture medium for screening microorganisms using RG-II as a source of carbon and energy has been produced as indicated in table 3. This is a mineral culture medium to which a solution of monomer RG-II is added and having a final concentration of 2 to 10 mg/ml. The cultures containing mushrooms have their contaminating bacteria removed by adding three antibiotics into the medium: penicillin G, streptomycin and tetracycline.

Samples have been taken from varied natural ecosystems (agricultural or forest soils, peat, composts, sludge from sewerage plants, decomposing fruit) and cultured between 25 and 37° C. on the mineral culture medium adjusted to 10 mg/ml in the monomer RG-II. Each time it has been observed that the microorganisms have grown, the cultures have been planted out several times on the same medium. This procedure initially makes it possible to isolate several cultures ensuring their growth on the RG-II medium. The degradation of the RG-II in the medium has been controlled in parallel by means of high-performance steric exclusion chromatography and only those cultures where this degradation has been observed in parallel with the growth of the microorganisms have been retained.

The microoganisms ensuring degradation of RG-II have been isolated after spreading the cultures in Pétri boxes on a gelosed medium obtained by adding 2% agarose into the culture medium (Table 3) and lo containing 2.5 mg/ml of monomer RG-II. After a week of incubation at 25° C., clones have been sampled and inoculated in the liquid culture medium so as to control their capacity to degrade RG-II.

3—Choice of Branches Degrading RG-II

Two fibrous mushroom branches were finally retained as they possessed the required properties:

1—Rapid growth and fully correlated with the reduction of the RG-II in the medium.

2—The disappearance of an amount of the RG-II was observed in parallel with a shift of its HP-SEC elution volume which indicated the presence of endo-hydrolase type degradation enzymatical activities.

3—The final level of degradation of the RG-II reached 70% with one culture week at 25° C.

These two cultures numbered E and K have been accordingly used for the production of enzymes for degrading RG-II and a study of the enzymatical modes of action. They are cultivated without agitation in contact with air at 25° C. in a liquid culture medium containing 5 mg/ml of RG-II in the presence of three antibiotics; penicillin G, streptpmycine and tetracycline.

EXAMPLE 7

Production of Enzymes for Degrading RG-II

The various species of Penicillium are known for their ability to produce and salt out in the culture media of enzymes for degrading polysaccharides. The capacity of two isolated branches to produce enzymes for degrading RG-II has been verified.

1—Search for Enzymes Able to Degrade RG-II in the Culture Floating Substance

The branches *P. daleae* LaV2 (File N° CNCM 1-1578) and *P. simplicissimum* IPV1 (File N° CNCM 1-1577) have been cultured at 25° C. on the medium containing 2.5 mg/ml of monomeric RG-II. After 96 hours of culture, 1 ml of the culture medium containing growing mycelium was taken and sterilely filtered on a 0.22 μm filter and then 2 mg/ml of native RG-II was added. The medium containing the degradation enzymes and the RG-II was placed to incubate at 25° C. and 25 μl fractions were taken to 0.20 and 45 hours and CES-HP analysed. The comparison between the elution profiles of the RG-II at different incubation times clearly revealed the absence of any degradation activities of the RG-II in the culture medium. These activities have therefore been sought in the cytoplasm and the periplasm of the mushrooms.

2—Production of Enzymes for Degrading RG-II in the Total Cellular Extracts of Mushrooms The aforesaid branches *P. daleae* LaV2 and *P. simplicissimum* IPVI have been cultured at 25° C. on 4 ml of a medium containing 6 mg/ml of monomeric RG-II. After 140 hrs of culture, the mycelium was recovered by hydroextraction prior to crushing (with glass balls) to 4° C. fir 4 min in a 50 mM MES/KOH buffer (morpholino-ethanesulfonic acid) adjusted to pH 6, added with 1 mM of PMSF (phenyl methyl sulfonyl fluoride) and 1 mM of DTT (dithiothreltol). The cellular supernatant has been recovered by centrifugating at 10,000 g×5 min.

Figure 8:
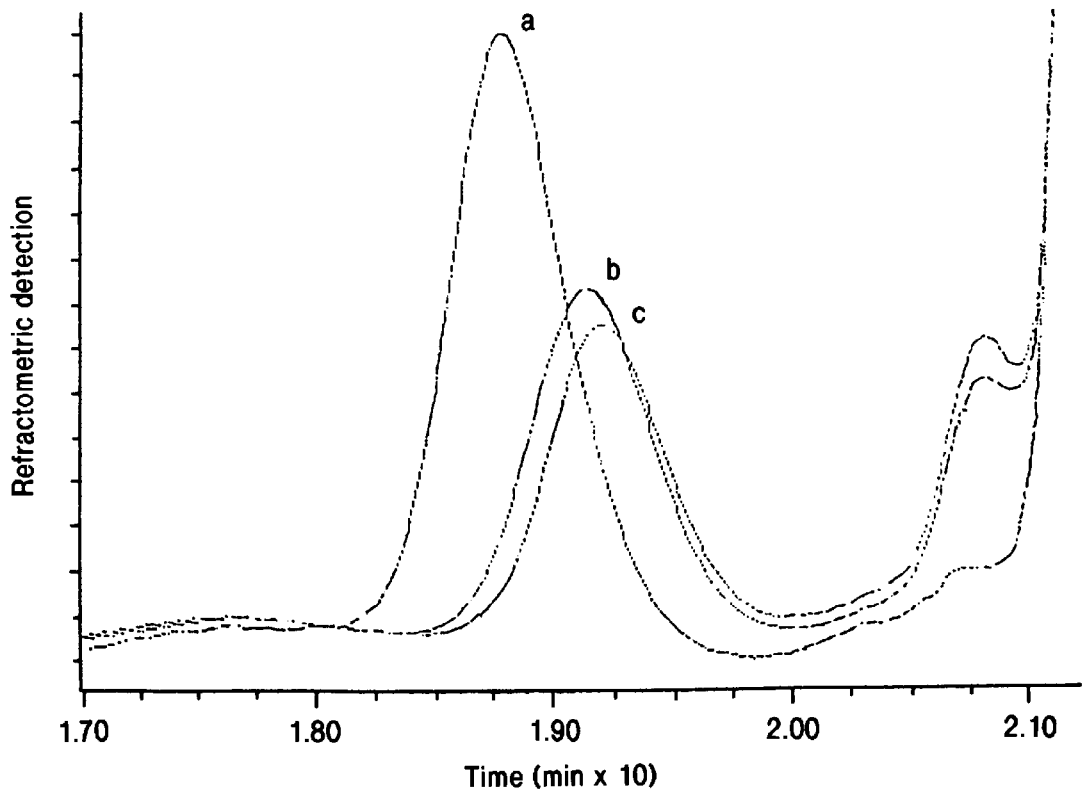
FIG. 8 illustrates the degradation of RG-II by a soluble cellular extract of *Penicillium simplicissimum* (1-1577). The spectrums a, b and c respectively correspond to native RG-II, RG-II after 24 hours and 48 hours of degradation.
Figure 9:
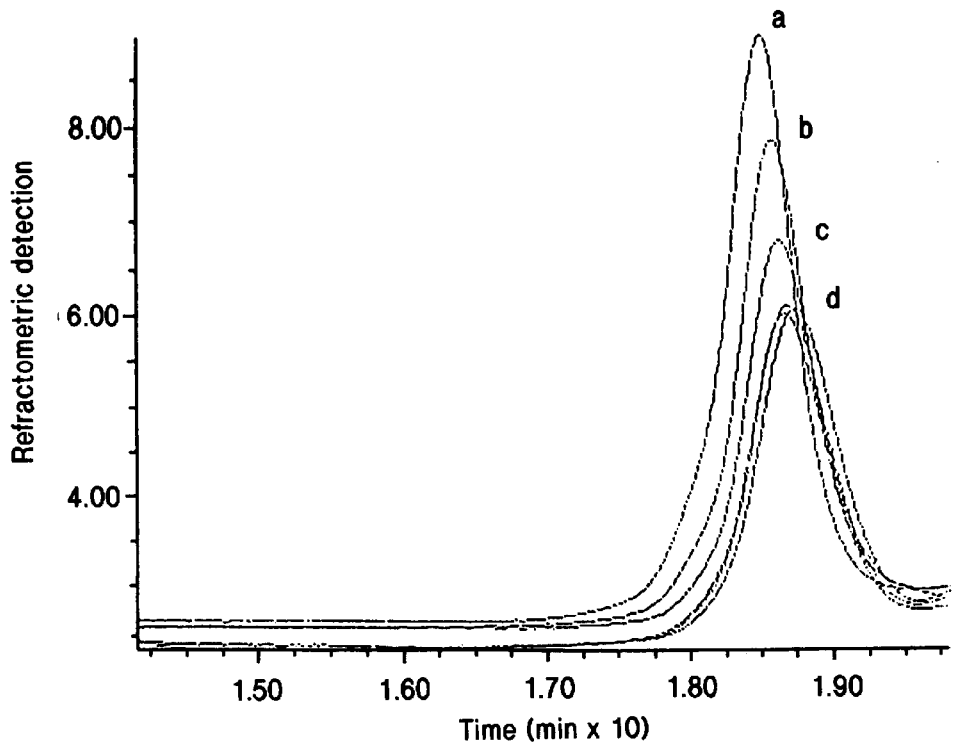
FIG. 9 illustrates the degradation of RG-II by a soluble cellular extract of the LaV2 branch (1-1578) (a: native RG-II, b: after 96 hours; c: after 168 hours, d: after 190 hours).

The presence of enzymes for degrading RG-II in the soluble cellular extract has been tested by adding 2.5 mg/ml of native RG-II to the surface substance after crushing and centrifugation, incubation at 25° C. and follow-up by CES-HP of degradation of the RG-II. The analysis of the profiles at 24 and 48 hours compared with the native RG-II (FIGS. 8 and 9) shows a high degradation (50%) of the RG-II from 24 hours which is continued until 48 hours so as to give a 40% residual molecule.

The enzymatical activities ensuring degradation of the RG-II are thus present in the soluble cellular extract and may therefore be obtained after crushing of the mushrooms. The two isolated branches of Penicillium are therefore good producers of enzymes able to degrade rhamnogalaturonane II.

EXAMPLE 8

Characterisation of the Activities for Degrading RG-II

The two isolated species of Penicillium produce enzymes which degrade the RG-II in the culture medium. The mode of action of these enzymes has been initially studied by following the degradation of the polysaccharide in the medium whilst the mushrooms were growing. This approach has the drawback of only being able to follow the RG-II fraction not assimilated by the mushroom, but does however account for the activities used and their mode of action.

1—Production of a Degradation Kinetics of RG-II by *Penicillium simplicissimum*

Figure 10:
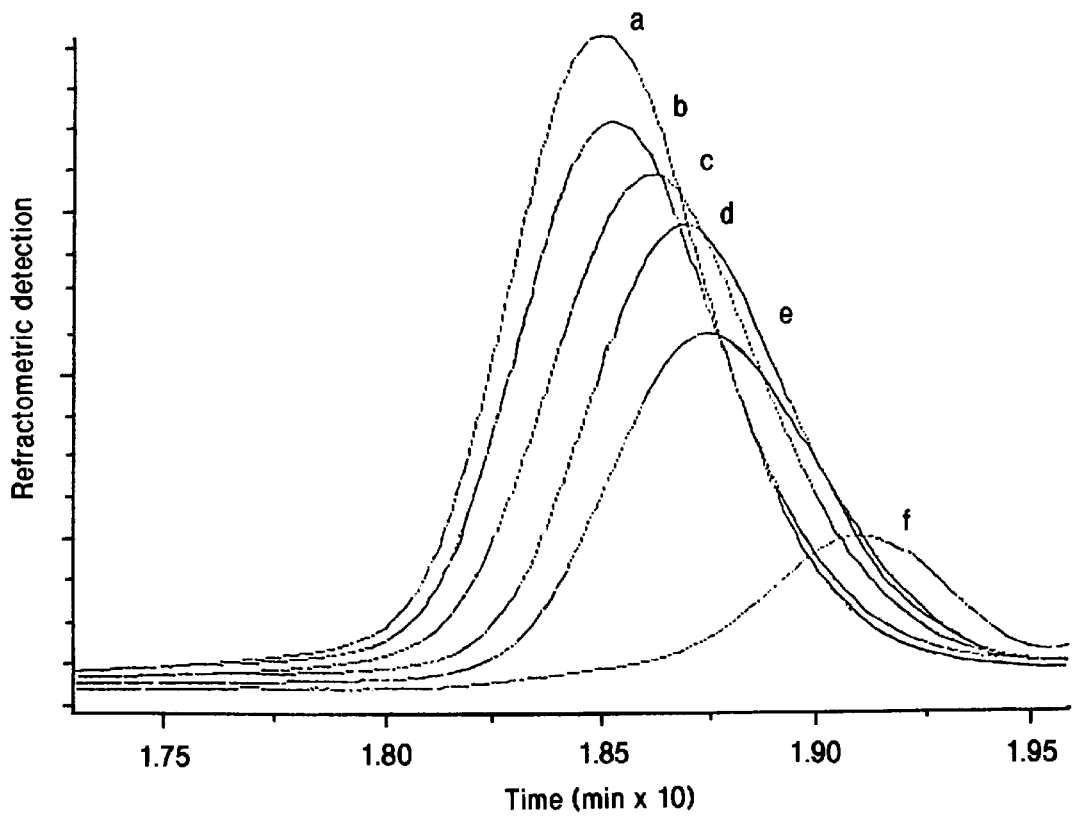
FIG. 10 illustrates the degradation followed by CES-HP chromatography of RG-II by a *Penicillium simplicissimum* (1-1577) culture. The curves a to f respectively represent the spectrum of native RG-II and the spectra of RG-II after 96 hours, 132 hours, 1268 hours, 192 and 400 hours of growth of the mushroom.

The IPVI *P. simplicissimum* source has been placed in an Erienmeyer culture at 25° C. on 10 ml of medium with 5 mg/ml of monomeric RG-II. 1 ml fractions were taken at 0.96, 132, 168 and 192 hrs. The pH of the medium was then readjusted to 5 by adding 20 μl of HCl 1 M. A next sampling was carried out at 360 hrs, the culture being finally halted after 400 hrs of incubation. Each sampling has been CES-HP analysed (FIG. 10) which makes it possible to follow up degradation whilst the mushrooms were growing. The various sampled fractions have been desalted on a Bio-Gel P-6 column (1×50 cm) balanced in a 100 mM, pH 4, sodium acetate buffer.

For each incubation time, a complete structural analysis of the RG-II fraction was made during degradation. This analysis includes:

The quantification of the degradation rate of the RG-II.

The determination of the neutral oses and uronic acids composition.

The determination of the types of links between the residues constituting the molecule.

The determination of the length of the homo-galacturonic chain.

All these analyses are able to show the state of the RG-II molecule for each sampling and thus follow up its time-degradation. These results give details of the enzymatical mode of degradation of the molecule over a certain period of time.

2—Production of a Degradation Kinetics of RG-II by *Penicillium Daleae*

Figure 11:
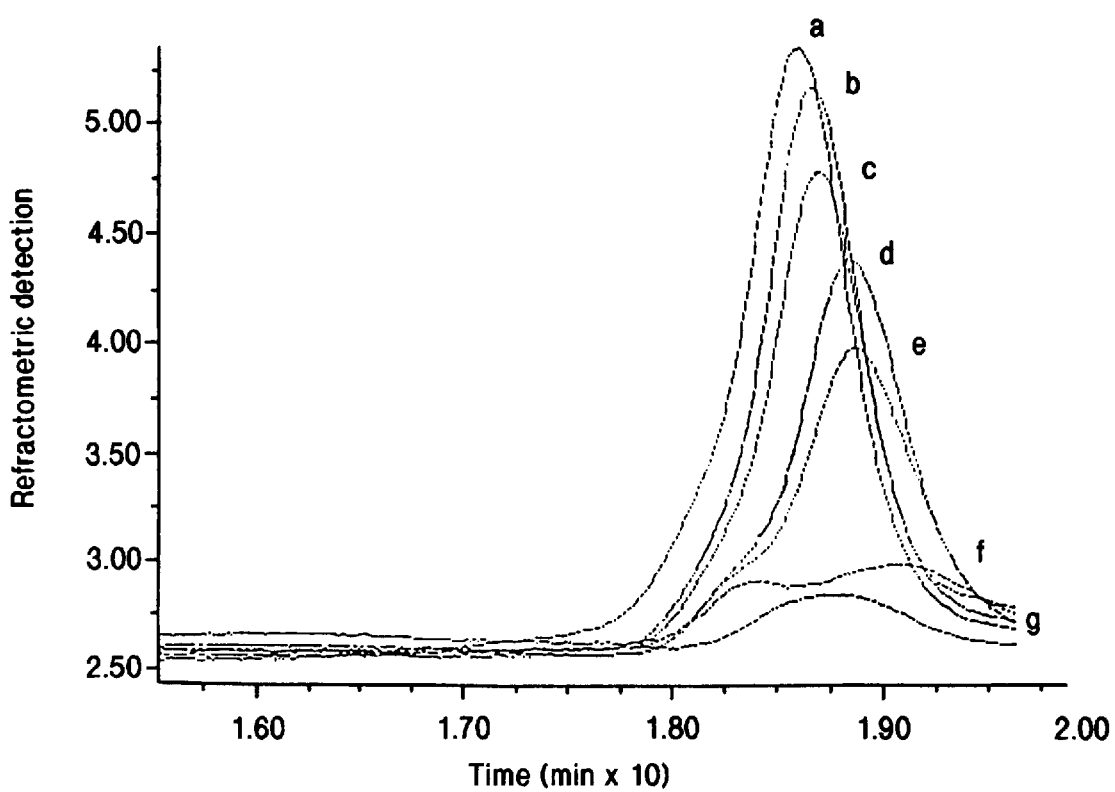
FIG. 11 illustrates the degradation of RG-II by a *P. daleae* culture (1-1578) followed by CES-HO chromatography at different times (a: native RG-II; b: 72 hrs; c: 120 hrs; d: 240 hrs; e: 264 hrs; f: 336 hrs; g: 384 hrs).

For following up the degradation of RG-II by *P. daleae* LaV2, 500 mg of a monomeric RG-II preparation have been previously saponified (2 hrs at 4° C. in 50 mM NaOH) and then reduced (6 hrs at 4° C. in the presence of 2.5 g of NaBH4) so as to mark the reducing extremity of the molecule. The LaV2 *P. daleae* branch has been placed in an Erienmeyer culture at 25° C. on a 6 ml medium with 5 mg/ml of saponified RG-II and reduced. 0.6 ml fractions have been taken at 0; 72, 120, 168, 240, 264, 336 and 384 hrs. Each sampling has been CES-HP analysed (FIG. 11) so as to follow up degradation whilst the mushrooms were growing. The sampled various fractions were desalted on a Superdex-75 HR column (1×30 cm) balanced to 0.6 ml/min in a 30 mM, pH 5.2, ammonium formiate buffer.

For each incubation time, a full structural analysis of the RG-II fraction was carried out during degradation. This analysis includes:

Quantification of the degradation rate of the RG-II.

Determination of the neutral oses and uronic acids composition in the form of trimethylsilylated derivatives after methanolysis.

The determination of the types of links between the residues constituting the molecule by means of methylation analysis including reduction of the uronic acids to trienthylborodeutetride lithium (Pellerin et al. 1995 Carbohydr. Res 277:135–143.

The determination of the length of the homo-galacturonic chain.

All these analyses are able to show the state of the RG-II molecule for each sampling and thus follow up its time-degradation. These results specifiy details of the enzymatical mode of degradation of the molecule over a certain period of time.

3—Mechanism of Degradation of RG-II

Figure 12:
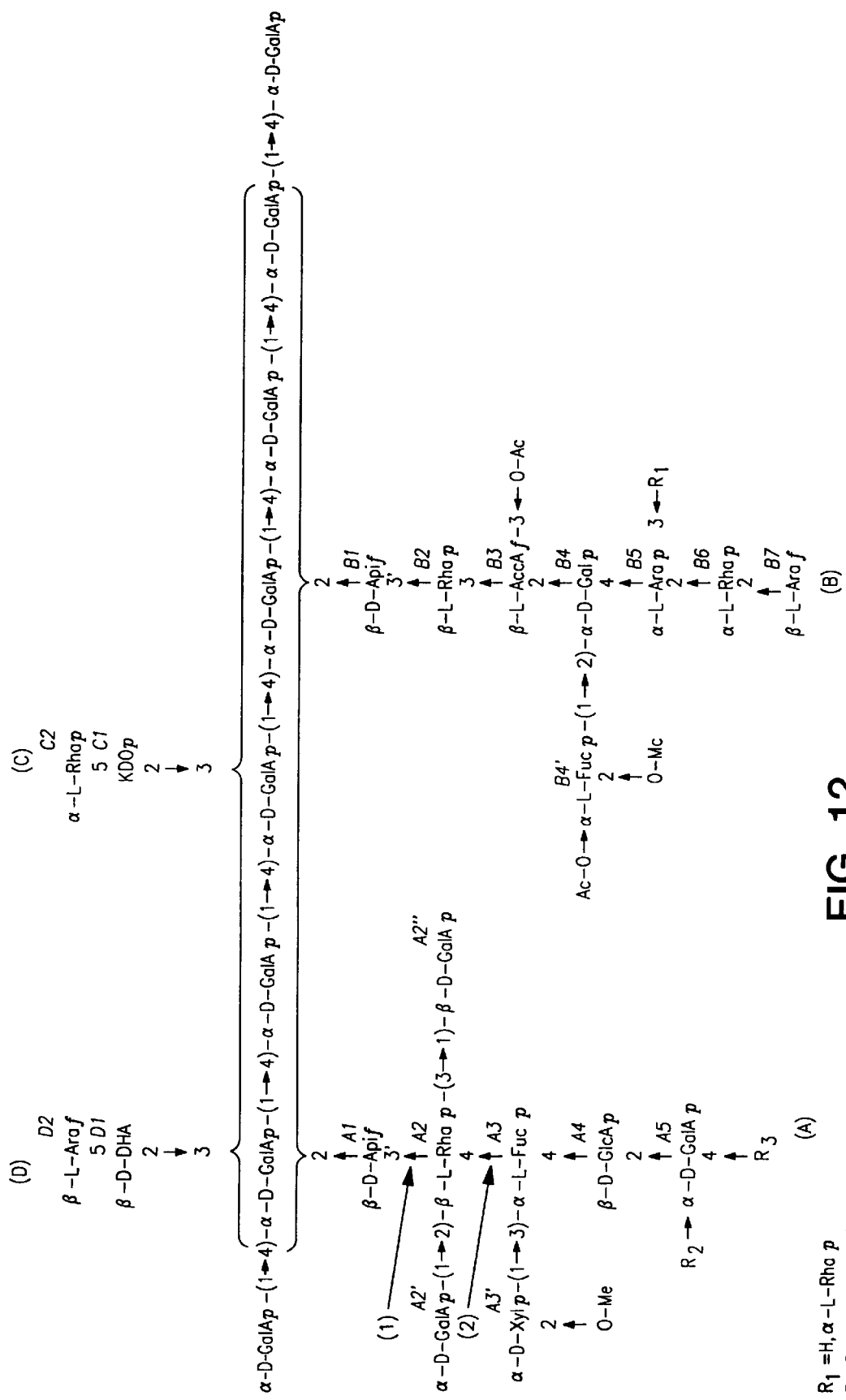
FIG. 12 represents the structure of FIG. 1 simplified. The potential enzyme cutting sites according to the present invention are indicated (arrows 1 and 2).

The analysis of the composition (tables 4 and 5) and the types of link for each residue present in the molecule (tables 6 and 7) make it possible to follow up the state of the residual molecule of the RG-II over a certain period of time and illustrate that the RG-II is degraded for the two Penicillium branches by a series of enzymes which act sequentially:

a) The first degradation stage consists of the rupture of the links between the trisubstituted β-L-rhamnose and the residues of α-L-fucose and β-D-apiose, which results in the loss of chain A (FIG. 12) which is assimilated by the mushroom. This stage occurs during the first days of culture in parallel with a slight shortening of the homo-galacturonic chain which moves from 8–9 to 7 residues on average and with a partial loss of the arabinofuranose (B7 and D2) and rhamnopyranose (C2) terminal residues.

b) The complete elimination of residues A2 to A5 of the chain A borne by the β-D-apiose residue seems to raise the resistance of the RG-LL molecule to the enzymatical degradations since a second degradation phase is then observed which is characterised by:

A significant shortening of the homo-galacturonic chain which passes to an average size of 4 residues of galacturonic acid, The loss of residue A1, The chain B, still inked to the homo-galacturonic chain by means of the β-D-apiose, undergoes modifications concerning its non-reducing terminal extremity, namely the quantitative loss of the terminal arabinofuranose residue and the loss of the residues of α-L-rhamnose (residues B6 and B7).

The Kdo and Dha residues seems to be partially affected by the enzymatical degradation.

All the degradations observed during this second phase can be obtained with the aid of known enzymes: β-D-apiosidase, β-L-arabinosidase, α-L-rhamnosidase, endo- or exo-polygalacturonase.

Figure 13:
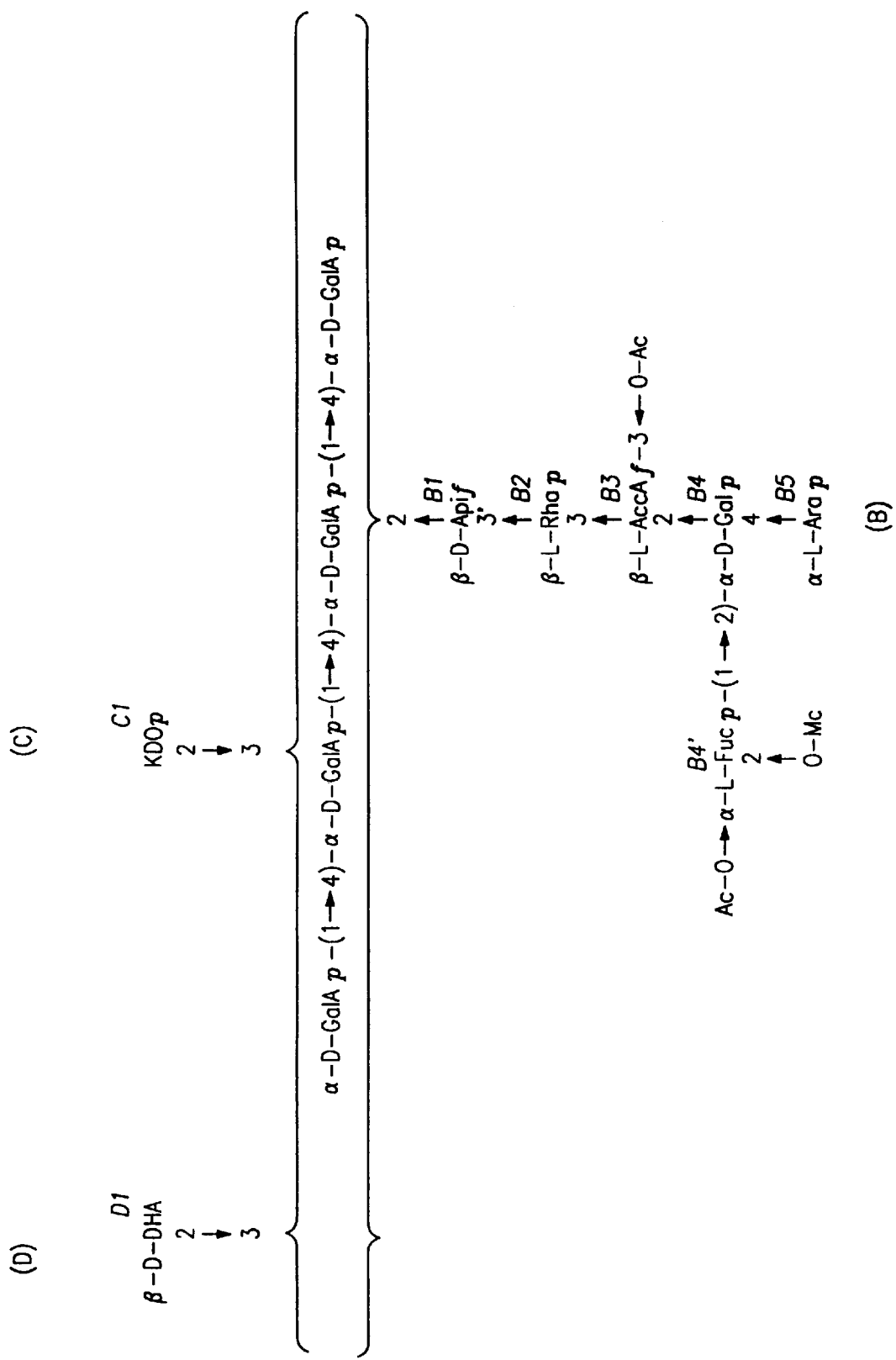
FIG. 13 represents the structure of the residual fraction of RG-II after it has been degraded by *Penicillium simplicissimum* and *Penicillium daleae*.

The residual molecule at the end of the mushroom growth quantitatively corresponds to chain B (residues B1 to B5), to the residues of Kdo (C1) and Dha (D1) borne by an oligosaccharide, average polymerisation acid degree 4, and represents 20 to 30% of the initial RG-II molecule (FIG. 13).

The first stage, which makes use of two endo- type enzymatical activities, is thus the stage enabling the RG-II molecule to be degraded. The quantitative freeing of the chain A in fact renders the molecule sensitive to the enzymes effect with known modes of action and which are frequently encountered in commercial enzymatical preparations.

The production of enzymes with endo-β-L-rhamnopyranosyl-(1→3')-D-apiofuranosyl hydrolase (1) and endo-α-L-fucopyranosyl-(1→4)-L-rhamnopyranolsyl hydrolase (2) type activities by LaV2 *P. daleae* and IPVI *P. simplicissimum* is therefore the determining stage which enables these mushrooms to grow by using the RG-II. It is therefore the use of these enzymes with endo-β-L-rhamnopyranosyl-(1→3')-D-apiofuranosyl hydrolase (1) and endo-α-L-fucopyranosyl-(1→4)-L-rhamnopyranosyl hydrolase (2) type activities which allows the thorough enzymatical degradation of the RG-II. The specificity of the activity (1) is high since the chain B is not affected by its hydrolytic activity, although it is connected to the homo-galacturonic chain by means of a rhamnosyl-apioside link of the same type. This behavioural difference of the activity (1) in relation to chains A and B can be explained as follows:

Either by the difference between the substituents of rhamnose: a chain linked at C3 in the case of B, a chain linked at C4 and two monosaccharides linked at C2 and C3 in the case of A.

Or by a different localisation of these two chains within the RG-II molecule.

The presence in an enzymatical preparation of either of these two activities allows the chain to be freed from the RG-II and thus raises the problem of non-degradability of the RG-II by the usual enzymes of pectinolytic preparations. In fact, the other enzymes allowing for a more thorough degradation of the RG-II occurs after the start of the chain A under the action of said enzymes. This second degradation stage brings in the following activity enzymes:

β-D-apiosidase

β-L-arabinosidase

α-L-rhamnosidase
endo-polygalacturonase
exo-polygalacturonase.

EXAMPLE 9

Obtaining a Dimeric RG-II Preparation and Degradation by *Penicillium daleae*

Figure 14:
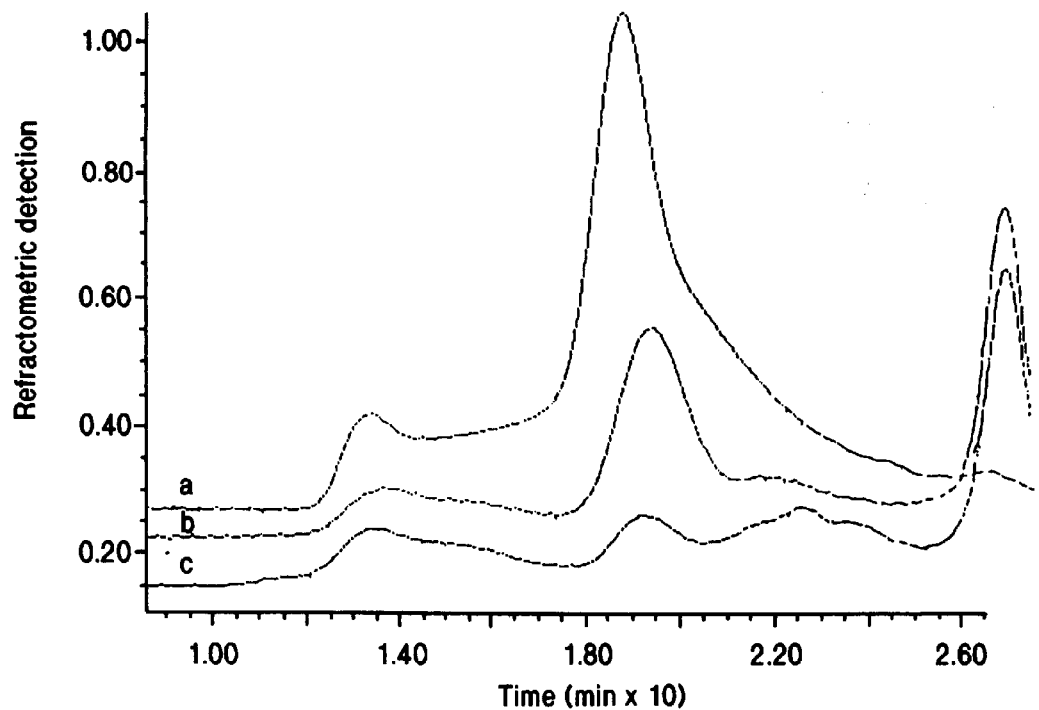
FIG. 14 illustrates the degradation of dimeric RG-II by a *Penicillium dateae* culture (1-1578). The spectra a to c respectively represent the spectrum of the dimeric native RG-II and RG-II after 168 and 300 hours of degradation.
Figure 15:
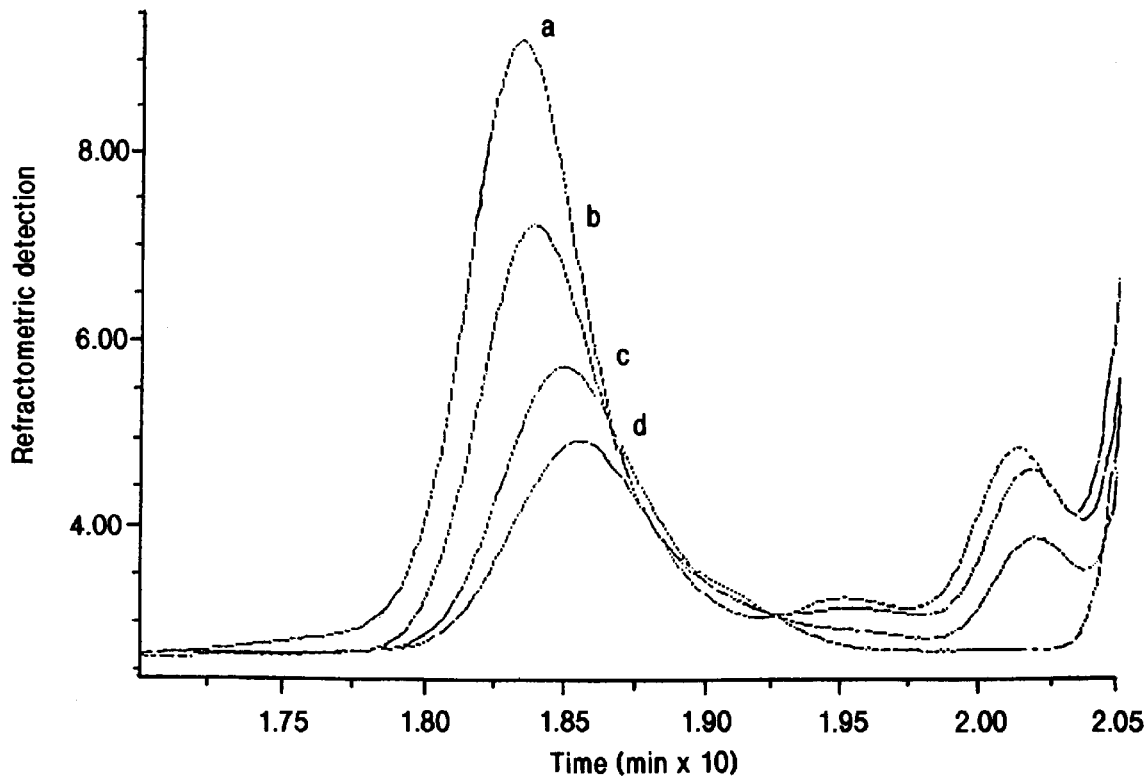
FIG. 15 illustrates the degradation followed by CES-HP chromatography of the RG-II purified by a total soluble cellular extract of *Penicillium simplicissimum* (1-1577). The spectra a to d respectively correspond to the initial RG-II and to the RG-II after 72 hours, 120 hours and 148 hours of incubation.

The *P. daleae* branch is placed in a culture on a medium containing a 5 mg/ml RG-II preparation obtained by passage of slops concentrates on Relite® DIAION® (example 2). This preparation contains about 60% of RG-II which appears in a dimeric form and shows the analysis on a Superdex-75 Hr column. The follow up by CLHP (FIG. 14) of the mushroom culture medium shows a high degradation of the RG-II. The contaminating substances with a higher molecular weight (mainly mannans present in the slops concentrates) are not degraded.

The isolated Penicillium branches on monomeric RG-II thus have the capacity to degrade the RG-II in a dimer form. The enzymes of the present patent application ate thus active on the two forms of the molecule.

EXAMPLE 10

Obtaining an Enzymatical Preparation Degrading RG-II

An enzymatical preparation containing the activities for degrading RG-II, in particular the endo-β-L-rhamnopyranosyl-(1→3')-D-apiofuranosyl hydrolase or endo-α-L-fucopyranosyl-(1→4)-L-rhamnopyranosyl hydrolase (2) type activities, has been obtained from an IPVI *P. simplicissimum* culture made up as follows:

120 ml culture medium containing 6 mg/ml of purified RG-II has been split into 8 Pétri boxes. The branch IPVI *P. simplicissimum* has been placed in a culture at 25° C. for 6 days. The mycelium (1.2 g by fresh weight) was then recovered by centrifugation prior to crushing as described above (example 3) in the 50 mM MES/KOH buffer adjusted to pH 6 containing 1 mM of PMSF and DTT. The total enzymatical extract (6 ml) was finally obtained by centrifugation and used for the following examples:

EXAMPLE 11

Degradation of RG-II Purified by the Enzymatical Extract of *P. simplicissimum*

The following mixture was incubated at 25° C. with 0.02% of NaN$_3$:

500 μl of 50 mM sodium acetate buffer

EXAMPLE 12

Degradation of the Polysaccharides of a Wine by the Enzymatical Extract of *P. simplicissimum*

The total enzymatical extract containing the enzymes for degrading RG-II, in particular the endo-β-L-rhamnopyranosyl-(1→3')-D-apiofuranosyl hydrolase or endo-α-L-fucopyranosyl-(1→4)-L-rhamnopyranosyl hydrolase type activities, has been tested for its capacity to degrade RG-II present in wines.

The total polysaccharides of a red wine (black Carignan variety) have been obtained by ultrafiltering the wine (2 ml) on a Centricon 30 membrane (Amicon, USA). The dialysis residue (100 μl) has been picked up by 1.9 ml of a 50 mM, pH 4.8; acetate buffer. The following tests have been carried out for incubation at 25° C. in the presence of 0.02% of NaN$_3$.

a: 200 μl of the dialysis residue containing the total polysaccharides of the wine
   5 μl of H$_2$O
   20 μl of a MES crushing buffer
b: 200 μl of the dialysis residue containing the total polysaccharides of the wine
   5 μl of H$_2$O
   20 μl of the total enzymatical extract of IPV1 *P. simplicissimum* obtained according to example 9.
c: 200 μl of the dialysis residue containing the total polysaccharides of the wine
   5 μl of Pectinex® Ultra Sp-L
   20 μl of the total enzymatical extract of IPVI *P. simplicissimum* obtained according to example 9.

Figure 16:
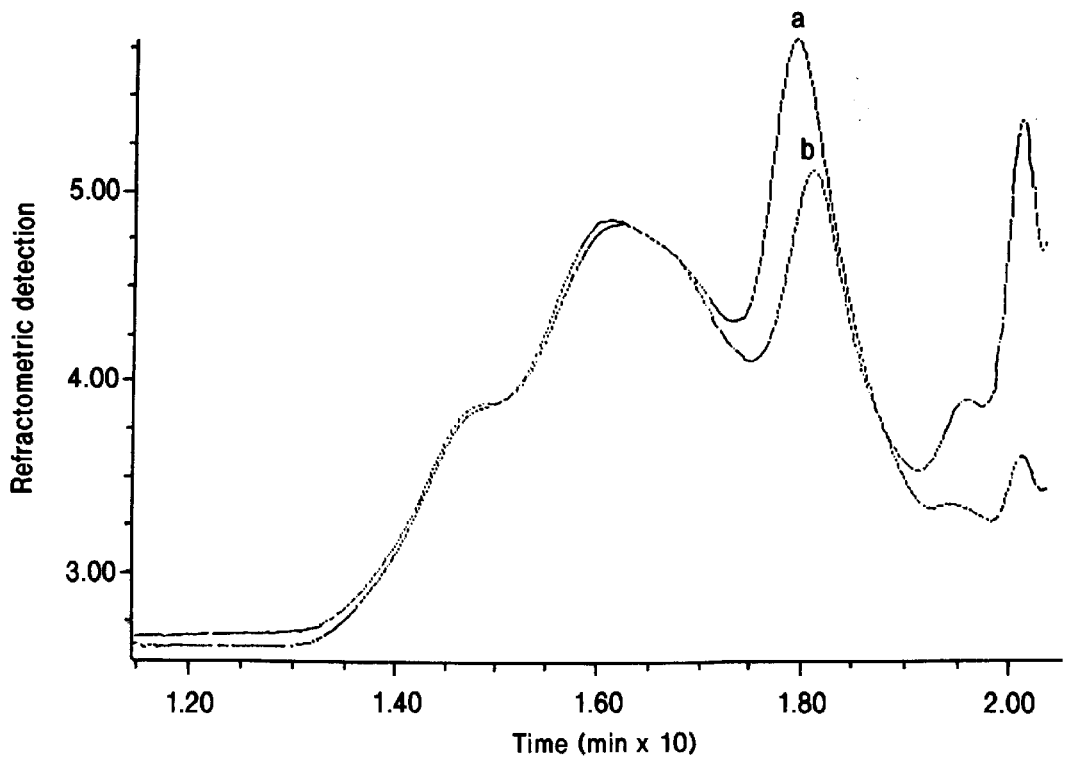
FIG. 16 is a comparison of the determined CES-HP polysaccharide profiles of a red wine (spectrum a) and after 48 hours of incubation in the presence of the IPVI enzyme extract (spectrum b).

After 48 hrs, 25 μl from each test have been taken and CES-HP analysed. The analysis of the results (FIGS. 16 and 17) shows:

The degradation of the RG-II of the wine (characteristic peak eluted at 18.2 mins) by the enzymatical extract of IPVI *P. simplicissimum* (FIG. 16).

Figure 17:
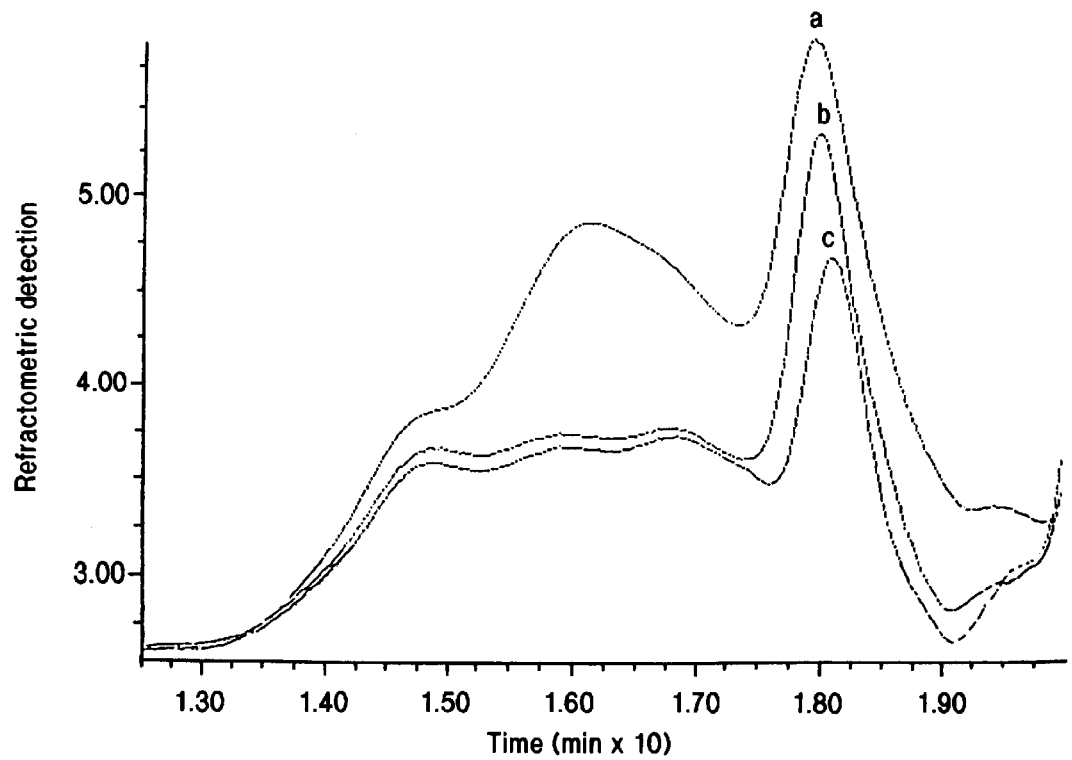
FIG. 17 is a CES-HP comparison of the polysaccharide profiles of a red wine (spectrum a) and after 48 hours of incubation in the presence of Pectinex® Ultra Sp L alone (spectrum b) or associated with the enzyme extract of the IPVI branch (spectrum c).

The degradation of the other polysaccharides of the wine (mannoproteins, arabinanes and arabinogalactanes) by the commercial Pectinex® Ultra Sp-L enzymatical preparation, whereas the characteristic peak of RG-II remains intact (FIG. 17).

The complementary effect of the two enzymatical preparations is confirmed (FIG. 17) by the degradation of all the polysaccharides of the wine in test c.

The total enzymatical extract of IPVI *P. simplicissimum* containing the endo-β-L-rhamnopyranosyl-(1→3')-D-apiofuranosyl hydrolase or endo-α-L-fucopyranosyl-(1→4)-L-rhamnopyranosyl hydrolase enzymes thus clearly contain the enzymatical activities not present in a commercial enzymatical preparation produced from *Aspergillus aculeatus* and rich in cellulolytic, hemicellulasic and pectinolytic activities and in particular rich in rhamnogalacturonase activity (Schols et al., 1990, Carbohydr. Res, 206, 105–115).

The addition of the enzymes conforming to the present invention and associated with other pectinolytic activities results in a more thorough degradation of the polysaccharides of the wine and thus allows for an improvement of filtering capacity and the prevention of the formation of colloidal and precipitates disturbances.

EXAMPLE 13

Degradation of the Polychaccharides of Apple Juice by the Enzymataical Extract of IPVI *P. simplicissimum*

Apple juice has been prepared from 1 kg of apples (Starking variety): the whole apples have been chopped into slices 1 cm thick with 1 g of ascorbic acid and 500 μl of a Rapidase® Liq (Gist Brocades, France) enzymatical preparation being added and left for 2 hrs under agitation at 50° C. The fruit has been liquefied under the action of the commercial enzymatical preparation, the juice then being obtained by centrifugation. The preparation of Rapidase® Liq contains high levels of pectinase (pectin, lyase, endo- and exo-polygalacturonose, rhamnogalacturonase, arabanase), hemicellulases (galactanases, xylanases) and cellulase activities.

1.5 ml of clear apple juice has been ultrtafiltered on a Centricon 30 membrane (Amicon, USA). The dialysis residue (100 µl) has been absorbed by 1.4 ml of a 50 mM, pH 4.8 acetate buffer and the following tests have been carried out for incubation at 25° C. in the presence of 0.02% NaN$_3$:

a: 200 µl of dialysis residue containing the total polysaccharides of the apple juice, 50 µl of H$_2$O b: 200 µl of the dialysis residue containing the total polysaccharides of the apple juice, 50 µl of the total enzymatical extract of IPV1 *P. simplicissimum.*

After 48 hrs, 25 µl from each test were sampled and CES-HP analysed.

Figure 18:
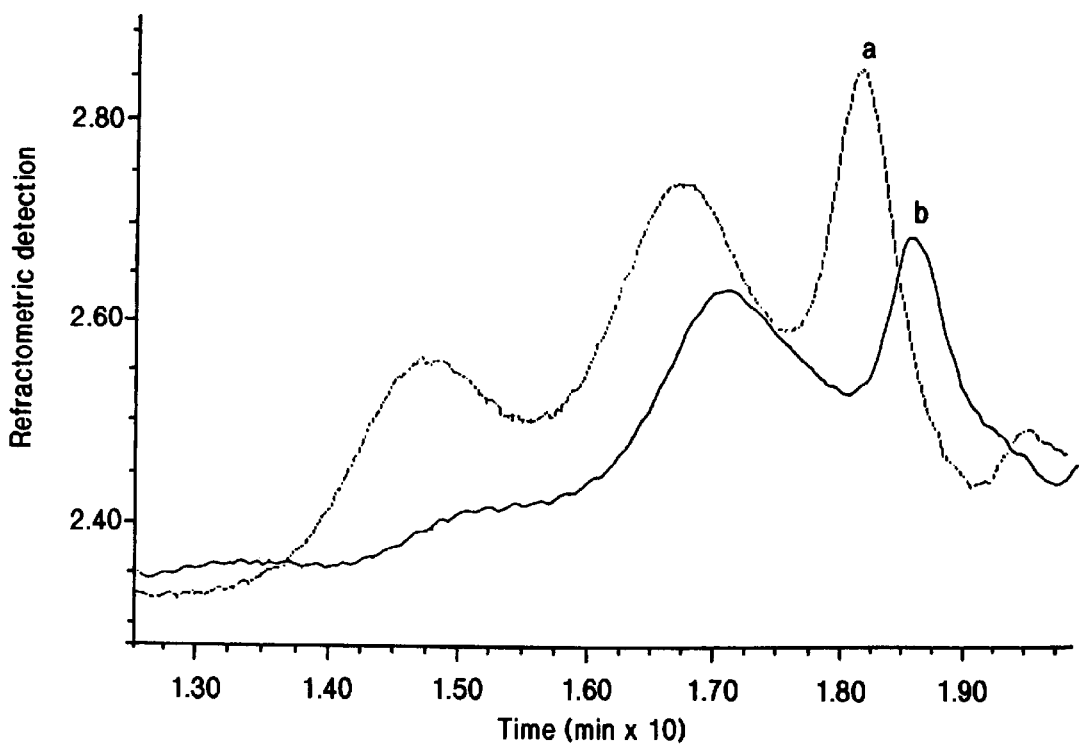
FIG. 18 is a CES-HP comparison of the polysaccharide profiles of apple juice obtained by the total liquefaction of the fruit by means of a Rapidase® Liq enzymatical preparation after 48 hours of incubation in the absence (spectrum a) and presence (spectrum b) of the enzymatical extract of the IPVI branch.
Figure 19A:
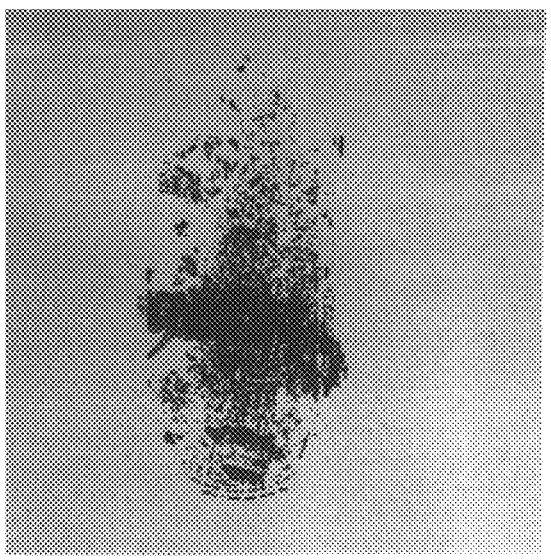
FIGS. 19A and 19B illustrate the degradation of beetroot tissues (FIG. 19A) by an enzymatical extract of the IPVI branch by comparing it with the reference.
Figure 19B:
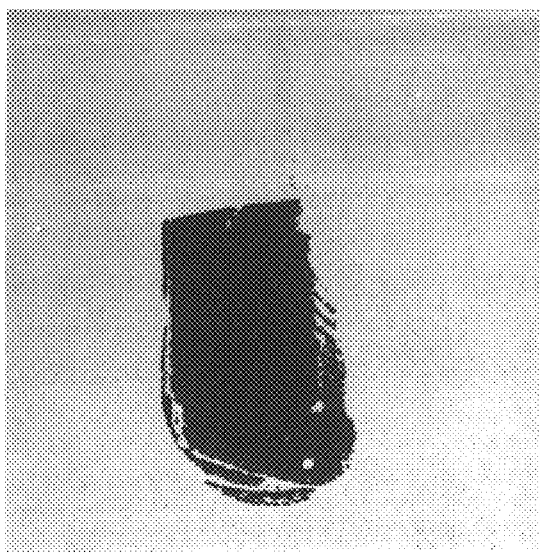
Figure 19C:
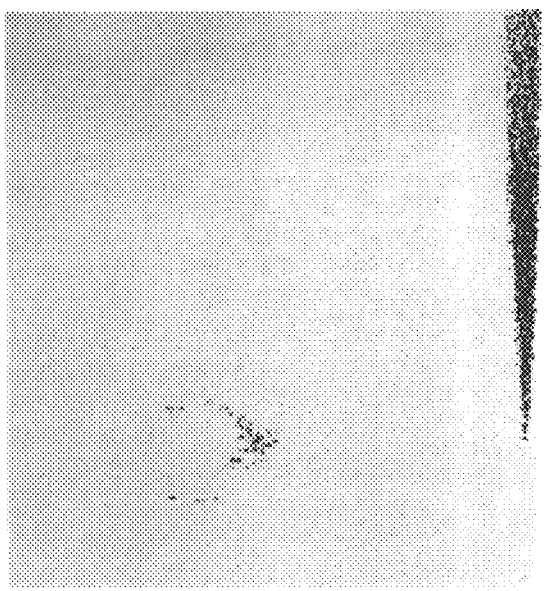
Figure 19D:
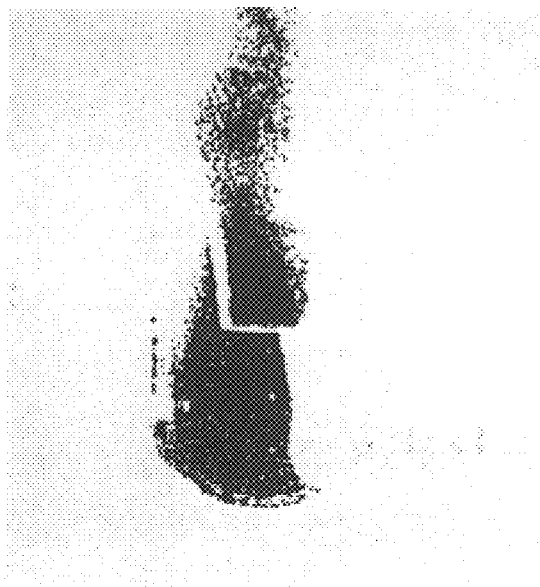

The analysis of the results (FIG. 18) shows the complementary effect of the enzymes for degrading RG-II since the addition of the enzymatical extract of IPV1 *P. simplicissimum* permits a thorough degradation of all the residual polysaccharides after treatment of the applies by the Rapidase® Liq preparation. In particular, the characteristic peak of RG-II (eluted at 18.2 min) undergoes a significant degradation. In addition, the degradation of the structures having a higher molecular weight resistant to the action of the enzymes present in Rapidase® Liq suggests that these fractions also contain RG-II fragments.

The total enzymatical extract of lPV1 *P. simplicissimum* in which the endo-β-L-rhamnopyranosyl-(1→3')-D-apiofuranosyl hydrolase or endo-α-L-fucopyranosyl-(1→4)-L-rhamnopyranosyl hydrolase type activities have been shown to clearly therefore contain enzymatical activities not present in a commercial enzymatical preparation produced from *Aspergillus niger* and described as possessing all the known cellulolytic, hemicellulastic, pectinolytic (including rhamnogalacturonase type) activities. The complementary and additional effect of the enzymes degrading RG-II is thus confirmed by this test.

EXAMPLE 14

Maceration of Fruits and Vegetables by the Enzymatical Extract of *P. simplicissimum*

The dissociation activity of the vegetable tissues of the total enzymatical extract of IPVI *P. simplicissimum* has been verified as regards the following fruits and vegetables:

Red beetroot

Carrot

"Bintge" potato

Golden apple.

158×4×2 mm fragments of each fruit or vegetable have been placed in a 2 ml 50 mM, pH 4.8, acetate buffer with the following being added:

200 µl of a crushing MES buffer for the references.

200 µl of the total enzymatical extract of IPV1 *P. simplicissimum* for the enzymatical tests.

The various tests have been carried out for incubatation at 25° C. in the presence of 0.02% of NaN$_3$ for 72 hours before being vigorously agitated in a vortex (2×10 sec) and photographed. The analysis of the results shows:

An almost total disintegration of the beetroot and carrot tissues (FIG. 19).

A macerating effect accompanied by the appearance of cells in suspension for the potato and apple (FIG. 20).

The total enzymatical extract of IPV1 *P. simplicissimum* containing the endo-β-L-rhamnopyranosyl-(1→3')-D-apiofuranosyl hydrolase or endo-α-L-fucopyranosyl-(1→4)-L-rhamnopyranosyl hydrolase type activities thus possesses an effect for dissociating vegetable tissues.

Conclusion

The enzymatical activities for degrading RG-II may therefore be used alone or in combination with other enzymes in a liquid phase or on solid supports and allow:

a high degree of degradation, such as 70%, of the RG-II in fruit and vegetable juices and their derivatives so as to improve filtering capacity, facilitate the preparation of concentrated juices, favour clarification phenomena and ensure good stability of the finished products.

the cleaning of micro- and ultra-filtering supports used for filtering fruit and vegetable juices and their derivatives.

These enzymatical activities favour the degradation of the cellular walls of plants and can therefore be used alone or in combination with other enzymes in all applications requiring maceration, liquefaction or the total or partial hydrolysis of plant tissues, especially:

in macerating type preparations for the production of fruit nectars, purées, jellies or fruit and vegetable concentrates and their derivatives, including wine;

in liquefying preparations for the production of juices and aromatic bases of fruits, vegetables and their derivatives, including wine, the production of beer;

for the production of pectins from vegetable residues; such as beetroot pulp, solid residues after fruit pressing;

for the production of foodstuffs for animals from plant material;

for the production of cellulose from plants for the textile industry (in particular from cotton), paper production;

for the production from plant residues of oligosacchardies with eliciting activity reactions for protecting plants and able to be used as phytosanitary products.

TABLE I

Composition of two RG-II fractions isolated from wine

| Molecule type | Fraction II | Fraction III |
|---|---|---|
|  | monomer | dimer |
| Proteins[a] | 0,6 | 0,6 |
| Uronic acids[a] | 36,9 | 39 |
| Neutral sugars[a] | 27,3 | 24,9 |
| Methanol[a] | 1,4 | 1,3 |
| Acetic acid[a] | 1,6 | 1,8 |
| Rhamnose[b] | 31,8 | 35,4 |
| 2-O—CH$_3$-Fucose[b] | 6,3 | 6,5 |
| Fucose[b] | 3,7 | 5,2 |
| 2-O—CH$_3$-Xylose[b] | 4,8 | 4,8 |
| Apiose[b] | 7,4 | 7,5 |
| Arabinose[b] | 25 | 23,7 |
| Galactose[b] | 19,1 | 15,8 |
| Aceric acid[b] | 1,2 | 2,2 |
| Galacturonic acid[b] | 38,2 | 37,2 |
| Glucuronic acid[b] | 3,3 | 3,4 |
| Kdo[b] | 4,4 | 5, |
| Dha[b] | 2,6 | 2,5 |

[a] % of dry material
[b] molar %

TABLE 2

Composition (in molar percent) and degree of purity of RG-II preparations obtained from various plant extracts and on different chromatographic supports

| Samples Supports used | Concentrated wine DEAE-Macroprep anion exchange | Apple Relite Diaion SP411 | Carrot Relite Diaion SP411 | Tomato Relite Diaion SP411 | Wine Relite Diaion SP411 | Grape must Amberlite XAD 2 | Concentrated slops Relite Diaion SP411 | Concentrated slops Carbon SA + |
|---|---|---|---|---|---|---|---|---|
| 2-O—Me-Fucosa | 6.3 | 5.0 | 6.2 | 6.1 | 1.1 | 2.0 | 1.8 | 2.0 |
| Rhamnose | 31.8 | 29.9 | 31.2 | 20.8 | 13.6 | 22.3 | 14.6 | 22.5 |
| Fucose | 3.7 | 10.8 | 7.9 | 14.7 | 1.7 | 6.0 | 1.7 | 1.7 |
| 2-O—Me-Xylose | 4.8 | 3.9 | 4.9 | 4.7 | 0.9 | 3.8 | 1.5 | 1.6 |
| Arabinose | 25.0 | 20.1 | 23.7 | 20.9 | 52.3 | 22.6 | 29.3 | 13.0 |
| Xylose | — | — | — | — | 0.9 | 14.9 | 0.8 | 1.1 |
| Apiose | 7.3 | 7.2 | 2.5 | 8.0 | 1.5 | 9.1 | 2.4 | 2.9 |
| Manose | 0.9 | 8.8 | 4.8 | 10.8 | 8.1 | 2.2 | 16.7 | 42.6 |
| Galactose | 19.1 | 12.0 | 17.2 | 14.2 | 15.0 | 3.0 | 27.7 | 11.8 |
| Glucose | 1.1 | 2.3 | 1.6 | — | 4.9 | | 3.4 | 0.9 |
| % of purity | 97 | 95 | 96 | 82 | 45 | 40 | 57 | 52 |

TABLE 3

Culture medium of fibrous mushrooms

Mineral medium:

| | | |
|---|---|---|
| $NH_4NO_3$ | 2 | g/l |
| $K_2HPO_4$ | 1 | g/l |
| $MgSO_4, 7H_2O$ | 0,5 | g/l |
| KCl | 0,5 | g,l |
| Sulfato de hieffo | 10 | g/l |

Heller solution:

| | | |
|---|---|---|
| $ZnSO_4$ | 1 | g/l |
| $MnSO_4, H_2O$ | 0,1 | g/l |
| $CuSO_4, 5H_2O$ | 0,03 | g/l |
| $MCl_2$ | 0,03 | g/l |
| $NiCl_2, 6H_2O$ | 0,03 | g/l |
| Kl | 0,01 | g,l |
| Boric acid | 1 | g/l |

TABLE 3-continued

Culture medium of fibrous mushrooms

Vitamins solution:

| | | |
|---|---|---|
| Vit B1 | 0,08 | g/l |
| Vit H | 0,08 | g/l |

Composition of the culture medium

| | |
|---|---|
| mineral medium | 1 ml |
| Heller solution | 1 µl |
| Vitamins solution | 1 µl |
| Streptomycin (50 mg/ml) | 2 µl |
| Tetracycline (5 mg/ml) | 2 µl |
| Penicillin (10,000 U/ml) | 10 µl |
| Polysaccharide | 5 mg/ml |

Culture embodied at room temperature (25° C.) in light.

TABLE 4

Composition (in % of the initial dry material) of RG-II during a degradation kinetics by *P. simplicissimum*

| | | Initial | 96 h | 132 h | 168 h | 192 h | 400 h |
|---|---|---|---|---|---|---|---|
| Neutral oses | | 28.2 | 28.5 | 23.1 | 19.1 | 18.5 | 10.3 |
| Uronic acids | | 40.4 | 35.3 | 25.9 | 18.1 | 16.4 | 9.9 |
| Neutral oses + Uronic acids | | 68.8 | 63.8 | 49.0 | 37.2 | 34.9 | 20.2 |
| Monosaccharides | Residue n° | | | | | | |
| 2-O—Me-Fucose | B4' | 2.1 | 2.4 | 2.1 | 2.0 | 2.1 | 2.0 |
| Rhamnose | A2, B2, B6, D2 | 9.4 | 9.1 | 7.2 | 6.4 | 5.4 | 2.9 |
| Fucose | A3 | 1.1 | 1.1 | 0.6 | 0.1 | 0.1 | 0.0 |
| 2-O—Me-Xilose | A3' | 1.4 | 1.6 | 1.2 | 0.1 | 0.0 | 0.0 |
| Arabinose | B5, B7, C2 | 6.2 | 6.0 | 5.5 | 5.0 | 4.5 | 1.5 |
| Apiose | A1, B1 | 2.2 | 2.7 | 2.5 | 2.4 | 2.2 | 1.4 |
| Galactose | A5, B4 | 5.5 | 5.0 | 3.5 | 2.7 | 2.4 | 2.5 |
| Galacturonic acid | A2', A2", poli-Gal A | 23.3 | 24.2 | 19.5 | 18.9 | 15.2 | 8.5 |
| Glucuronic acid | A4 | 3.2 | 3.0 | 1.8 | 0.3 | 0.2 | 0.0 |
| average dp of homogalacturonic chain | | 8 a 9 | 7 a 8 | 7 | 6 a 7 | 6 | 4 |
| Residual molecule % | | 100 | 93 | 71 | 54 | 51 | 29 |

TABLE 5

Composition of n° of residues of RG-II during a degradation kinetics by *Penicillium daleae*

| | Initial | 120 h | 168 h | 240 h | 264 h | 336 h | 384 h |
|---|---|---|---|---|---|---|---|
| Rhamnose | 4.0 | 3.2 | 3.0 | 2.6 | 2.1 | 0.7 | 0.2 |
| 2-O—CH$_3$-Fucose | 1.0 | 1.0 | 1.0 | 0.8 | 0.8 | 0.2 | 0.1 |
| Fucose | 1.0 | 1.0 | 1.0 | 0.7 | 1.0 | 0.5 | 0.6 |
| 2-O—CH$_3$-Xilose | 1.0 | 1.0 | 1.0 | 0.5 | 0.3 | | |
| Apiose | 2.0 | 2.0 | 1.9 | 1.7 | 1.5 | 0.4 | 0.2 |
| Arabinose | 3.0 | 2.6 | 2.2 | 1.8 | 1.4 | 0.4 | 0.2 |
| Galactose | 2.0 | 1.8 | 1.3 | 1.1 | 0.9 | 0.2 | 0.2 |
| Galacturonic acid | 10.5 | 10.5 | 7.9 | 7.5 | 7.7 | 4.1 | 4.0 |
| Glucuronic acid | 1.0 | 1.4 | 0.8 | 0.3 | 0.3 | | |
| Acetic acid | 0.6 | 0.6 | 0.6 | 0.6 | 0.6 | 0.3 | 0.2 |
| Kdo | 0.9 | 1.9 | 0.9 | 0.5 | 0.9 | 0.7 | 0.6 |
| Dha | 0.7 | 0.11 | 0.3 | 0.3 | 0.6 | 0.6 | 0.5 |
| Total | 27.7 | 27.0 | 21.9 | 18.3 | 18.1 | 8.1 | 6.8 |
| average dp of homogalacturonic chain | 8.5 | 8.0 | 8.0 | 7.5 | 6.0 | 4.5 | 3.5 |
| Residual molecule % | 100 | 97 | 79 | 66 | 65 | 29 | 25 |

TABLE 6 analysis of methylation and links of the residues constituting the RG-II molecule at the time of its degradation by *P. simplicissimum*

| Methyl ether | Link type | Residue | Initial | 96 h | 132 h | 160 h | 192 h | 400 h |
|---|---|---|---|---|---|---|---|---|
| 2,3,4 - Rha[a] | Rhap(1→[b] | D2 B6 | 1.3 | 1.45 | 1.0 | 1.1 | 0.7 | 0.2 |
| 3,4 - Rha | →2)-Rhap-(1→ | B6 | 0.8 | 0.5 | 0.5 | 0.8 | 0.8 | 0.15 |
| 2,4 - Rha | →3)-Rhap-(1→ | B2 | 1.0 | 1.0 | 1.0 | 1.0 | 1.0 | 1.0 |
| Rha | →2,3,4)-Rhap-(1→ | A2 | 1.0 | 0.85 | 0.7 | 0.1 | 0 | 0 |
| 2,3,4 - Fuc | 2-O—Me-Fucp-(1→ | B4' | 0.7 | 0.7 | 0.7 | 0.7 | 0.6 | 0.6 |
| 2 - Fuc | →3,4)-Fucp-(1→ | A3 | 0.6 | 0.6 | 0.4 | 0.1 | 0 | 0 |
| 2,3 - Api | →3')-Api-(1→ | B1 A1 | 2.0 | 2.0 | 2.0 | 1.95 | 1.7 | 0.8 |
| 2,3,5 - Ara | Ara*f*-(1→[b] | C2 B7 | 1.2 | 1.4 | 1.0 | 1.0 | 0.8 | 0 |
| 2,3,4 - Ara | Arap-(1→ | B5 | 0.1 | 0.2 | 0.2 | 0.1 | 0.15 | 0.3 |
| 3,4 - Ara | →2)-Arap-(1→ | B5 | 0.2 | 0.4 | 0.55 | 0.7 | 0.7 | 0.4 |
| 4 - Ara | →2,3)-Arap-(1→ | B5 | 0.7 | 0.5 | 0.3 | 0.1 | 0 | 0 |
| 2,3,4 - Xil | 2-O—Me-Xilp-(1→ | A3' | 0.6 | 0.6 | 0.4 | 0.1 | 0 | 0 |
| 2,3,4,6 - Gal | Galp-(1→ | A5 | 0.5 | 0.45 | 0.1 | 0.05 | 0 | 0 |
| 3,6 - Gal | →2,4)-Galp-1(→ | B4 | 1.1 | 1.0 | 1.0 | 1.0 | 1.0 | 0.95 |
| 2,6 - Gal | →3,4)-Galp-(1→ | A5 | 0.45 | 0.4 | 0.3 | 0.08 | 0 | 0 |

The results are given in molar ratios calculated on the basis of 1 residue of →3)Rhap-(1→, residue N° B2 in the RG-II molecule and which remains constant during degradation.
[a]2,3,4-Me3-Rha = 1.5-di O-acetly-2,3,4-tri-O-rhamnitol, etc.
[b]p = pyranose,
f = furanose

TABLE 7

Analysis of methylation and links of the residues constituting RG-II during a degradation kinetics by *Penicillium daleae*

| Methyl ether | Link | Initial | 72 h | 120 h | 168 h | 240 h | 264 h |
|---|---|---|---|---|---|---|---|
| 2,3,4 - Rha | Rhap→ | 1.4 | 1.2 | 1 | 1.2 | 1.2 | 1.2 |
| 3,4 - Rha | →2-Rhap→ | 1.1 | 0.7 | 0.5 | 0.4 | 0.3 | 0.4 |
| 2,4 - Rha | →3-Rhap→ | 1 | 1 | 1 | 1 | 1 | 1 |
| 3 - Rhap | →2,4-Rhap→ | 0.4 | 0.1 | 0.3 | | | |
| Rha | →2,3,4-Rhap→ | 1.2 | 1.2 | 1.2 | 1.1 | 0.8 | 0.3 |
| 2,3,4 - Fuc | 2-O—CH$_3$-Fuc→ | 0.8 | 0.7 | 0.7 | 0.8 | 0.7 | 0.8 |
| 2 - Fuc | →3,4-Fuc→ | 0.6 | 0.7 | 0.7 | 0.6 | 0.3 | 0.2 |
| 2,3,4 - Xil | 2-O—CH$_3$-Xil→ | 0.6 | 0.6 | 0.5 | 0.5 | 0.3 | 0.1 |
| 2,3 - Api | →3'-Api-→ | 2.2 | 2.2 | 2.3 | 2.2 | 2.2 | 1.8 |
| 2,3,5 - Ara | Ara*f*→ | 1.6 | 1.4 | 1.1 | 1.3 | 0.8 | 0.8 |
| 3,4 - Ara | →2-Arap→ | 0.3 | 0.3 | 0.3 | 0.3 | 0.5 | |
| 4 - Ara | →2,3-Arap→ | 0.6 | 0.7 | 0.6 | 0.6 | 0.4 | 0.2 |
| 2,3,4,6 - Gal | Galp→ | 0.5 | 0.5 | 0.5 | 0.4 | 0.3 | 0.2 |
| 2,6 - Gal | →3,4-Galp→ | 0.6 | 0.6 | 0.5 | 0.5 | 0.4 | 0.3 |
| 3,6 - Gal | →2,4-Galp→ | 1.0 | 1.2 | 1.1 | 1.1 | 1.0 | 0.9 |
| 3 - Acer | →2-AcerA→ | 0.5 | 0.5 | 0.3 | 0.5 | 0.6 | 0.6 |
| 2,3,4 - GalA | GalpA→ | 2.6 | 3.0 | 3.0 | 2.6 | 1.9 | 1.4 |
| 2,3 - GalA | →4-GalpA→ | 2.0 | 2.3 | 2.1 | 1.8 | 1.7 | 1.5 |
| 2 - GalA | →3,4-GalpA→ | 1.5 | 1.5 | 1.5 | 1.5 | 1.3 | 1.3 |
| 3 - GalA | →2,4-GalpA→ | 1.1 | 1.2 | 1.3 | 1.3 | 1.8 | 1.6 |

TABLE 7-continued

Analysis of methylation and links of the residues constituting RG-II during a degradation kinetics by *Penicillium daleae*

| Methyl ether | Link | Initial | 72 h | 120 h | 168 h | 240 h | 264 h |
|---|---|---|---|---|---|---|---|
| GalA | →2,3,4-GalpA→ | 0.8 | 0.9 | 0.8 | 0.7 | 0.3 | 0.2 |
| 1,2,3,5 - GalA | →4-GalpA reduc. | 1.0 | 0.9 | 0.8 | 0.7 | 0.7 | 0.8 |
| 2,3,4 - GlcA | GlcpA→ | | 0.2 | | | | |
| 3,4 GlcA | →2-GlcpA→ | 1.1 | 1.4 | 1.3 | 1.1 | 0.6 | 0.4 |

The results are given on the basis of 1 residue of →3)Rhap-(1→, residue N° B2 in the RG-II molecule and which remains constant during degradation.
2,3,4 - Rhm = 1.5-di-O-acetyl-2,3,4-tri-O-methyl-rhamnitol, etc.

What is claimed is:

1. A total enzymatical extract having at least one activity selected from the group consisting of endo-β-L-rhamnopyranosyl-(1-3)-D-apiofuranosylhydrolase activity and endo-L-1-fucopyranosyl-(1-4)-L-rhamnopyranosylhydrolase activity for degrading rhamnogalacturonane(RG-II) and its derivatives wherein said isolated enzyme is produced by a penicillium strain selected from the group consisting of strain No. I-1577 (IPV) and strain I-1578 (LAV2) deposited at the National Collection of Microorganism Cultures at Institut Pasteur.

2. An isolated extract according to claim 1, characterised in that it has an endo-β-L-rhamnopyranosyl-(1→3')-D-apiopfruranosyl hydrolase.

3. An isolated extract according to claim 1, characterised in that it has an endo-α-I-fucopyranosyl-(I→4)-L-rhamnopyranosyl hydrolase activity.

4. A method for improving the filtering capacity for the preparation of concentrated fruits or flavor clarification comprising adding to the concentrated fruits or flavor clarification the extract of claim 1.

5. The isolated extract of claim 1, wherein the strain is No. 1-1578 (LAV 2) deposited at the National Collection of Microorganism Cultures at Institute Pasteur.

6. A process for the preparation of an extract of claim 1, comprising cultivating a Penicillium strain selected from the group consisting of the strain No. 1577 (IPV) and the strain No. I-1578 (LAV2) deposited at the National Collection of Microorganism Cultures at Institut Pasteur in a culture medium to produce an enzyme and recovering said enzyme from the culture supernatant of said penicillium strain.

* * * * *